United States Patent
Okumura et al.

(10) Patent No.: US 10,134,564 B2
(45) Date of Patent: Nov. 20, 2018

(54) CHARGED PARTICLE BEAM DEVICE

(71) Applicant: HITACHI HIGH-TECHNOLOGIES CORPORATION, Minato-ku, Tokyo (JP)

(72) Inventors: Taiga Okumura, Tokyo (JP); Takashi Ohshima, Tokyo (JP); Yuusuke Oominami, Tokyo (JP); Minami Shouji, Tokyo (JP); Akiko Hisada, Tokyo (JP); Akio Yoneyama, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 59 days.

(21) Appl. No.: 15/527,562

(22) PCT Filed: Nov. 26, 2015

(86) PCT No.: PCT/JP2015/083146
§ 371 (c)(1),
(2) Date: May 17, 2017

(87) PCT Pub. No.: WO2016/084872
PCT Pub. Date: Jun. 2, 2016

(65) Prior Publication Data
US 2017/0330724 A1    Nov. 16, 2017

(30) Foreign Application Priority Data
Nov. 28, 2014  (JP) .................................. 2014-240748

(51) Int. Cl.
*H01J 37/244* (2006.01)
*H01J 37/20* (2006.01)
(Continued)

(52) U.S. Cl.
CPC ............. *H01J 37/28* (2013.01); *H01J 37/20* (2013.01); *H01J 2237/0245* (2013.01); *H01J 2237/20* (2013.01); *H01J 2237/20214* (2013.01)

(58) Field of Classification Search
CPC .... H01J 37/28; H01J 37/20; H01J 2237/0245; H01J 2237/20; H01J 2237/20214
(Continued)

(56) References Cited

U.S. PATENT DOCUMENTS

| 5,278,408 A | 1/1994 | Kakibayashi et al. |
| 6,054,712 A * | 4/2000 | Komardin ............. A61B 6/483 250/363.06 |

(Continued)

FOREIGN PATENT DOCUMENTS

| JP | 61-263035 A | 11/1986 |
| JP | 4-337236 A | 11/1992 |

(Continued)

OTHER PUBLICATIONS

Office Action dated Dec. 12, 2017 for Japanese patent application No. 2014-240748 with machine translation.
(Continued)

*Primary Examiner* — Nicole Ippolito
(74) *Attorney, Agent, or Firm* — Miles & Stockbridge P.C.

(57) ABSTRACT

Provided is a charged particle beam device including a charged particle optical column that irradiates a specimen with a primary charged particle beam, and a specimen base rotating unit that is capable of rotating the specimen base in a state of an angle formed by a surface of the specimen base and an optical axis of the primary charged particle beam being inclined to a non-perpendicular angle, in which the specimen base is configured to include a detecting element that detects a charged particle scattered or transmitted inside the specimen, and transmitted charged particle images of the specimen corresponding to each angle is acquired by irradiating the specimen in a state of the specimen base rotating unit being rotated at a plurality of different angles.

15 Claims, 28 Drawing Sheets

(51) Int. Cl.
*H01J 37/26* (2006.01)
*H01J 37/28* (2006.01)

(58) Field of Classification Search
USPC ...... 250/396 R, 397, 440.11, 441.11, 442.11,
250/443.1, 492.1, 492.2, 492.21, 492.23,
250/492.3
See application file for complete search history.

(56) References Cited

U.S. PATENT DOCUMENTS

| | | |
|---|---|---|
| 8,710,439 B2 | 4/2014 | Ominami et al. |
| 9,508,527 B2 * | 11/2016 | Ominami ................. H01J 37/16 |
| 2004/0238752 A1 * | 12/2004 | Tanba ................... H01J 37/244 |
| | | 250/396 R |
| 2012/0235035 A1 * | 9/2012 | Nagaoki ................. H01J 37/09 |
| | | 250/307 |

FOREIGN PATENT DOCUMENTS

| | | |
|---|---|---|
| JP | 10-283978 A | 10/1998 |
| JP | 2011-065912 A | 3/2011 |
| JP | 2012-155870 A | 8/2012 |
| JP | 2012-221766 A | 11/2012 |
| JP | 2013-134978 A | 7/2013 |
| JP | 2014-072110 A | 4/2014 |

OTHER PUBLICATIONS

Office Action dated May 8, 2018 for Japanese patent application No. 2014-240748 with machine translation.

* cited by examiner

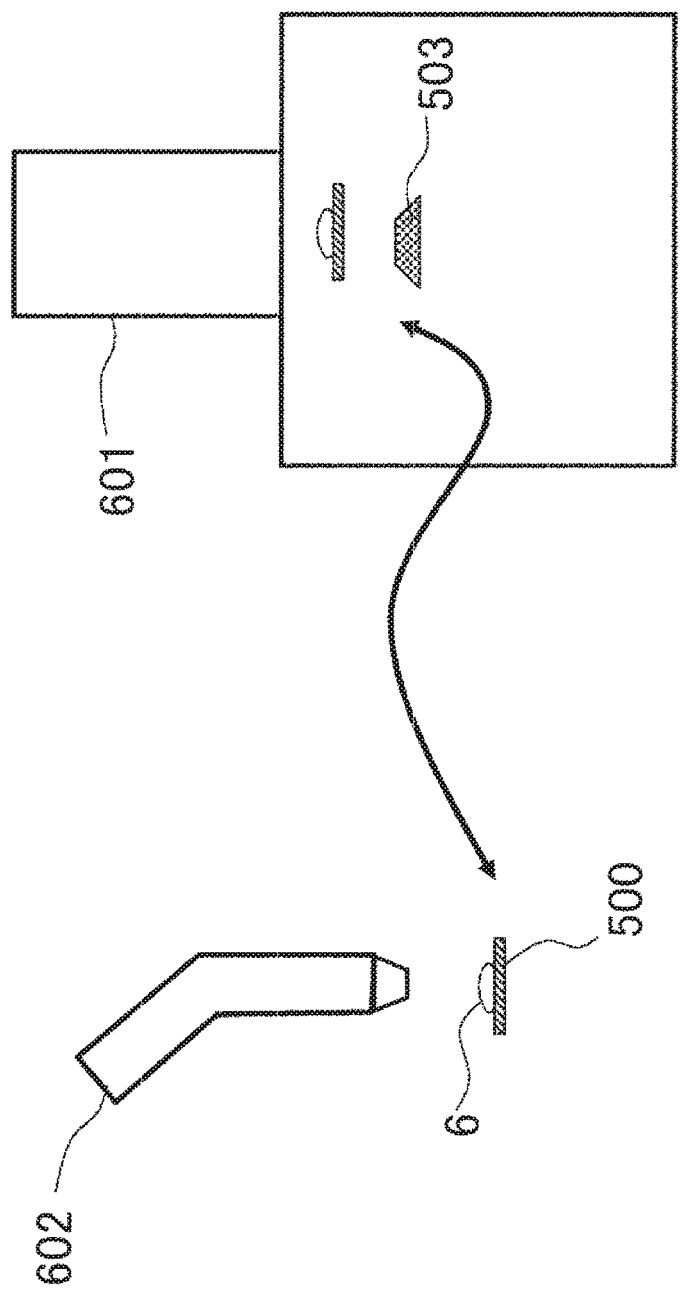
[FIG. 1]

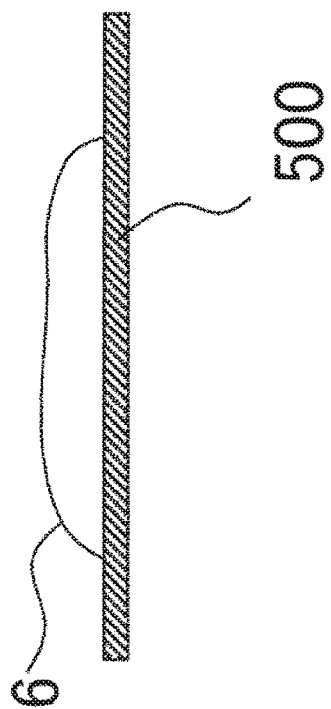
[FIG. 2]

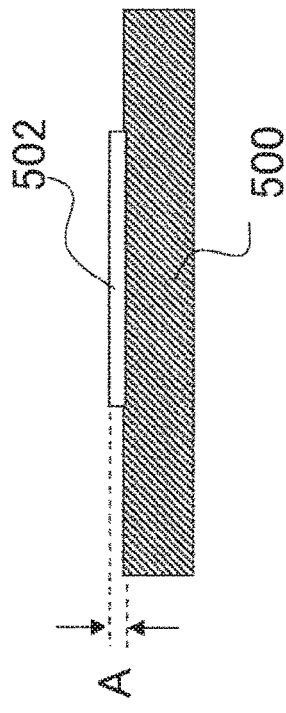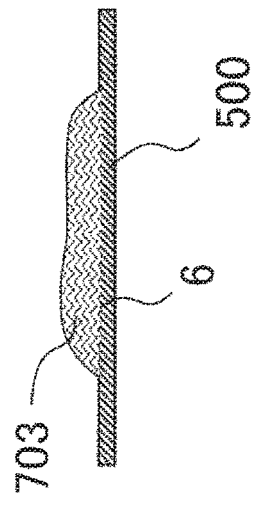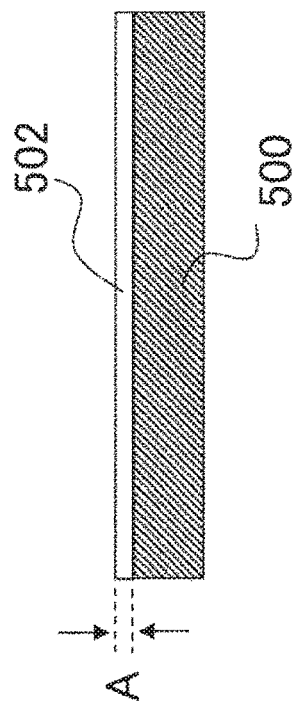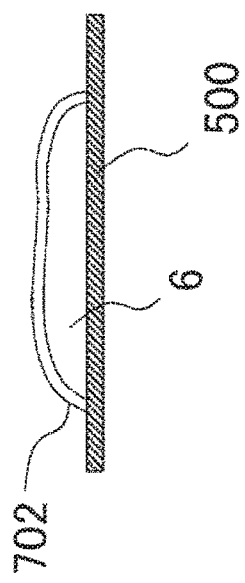

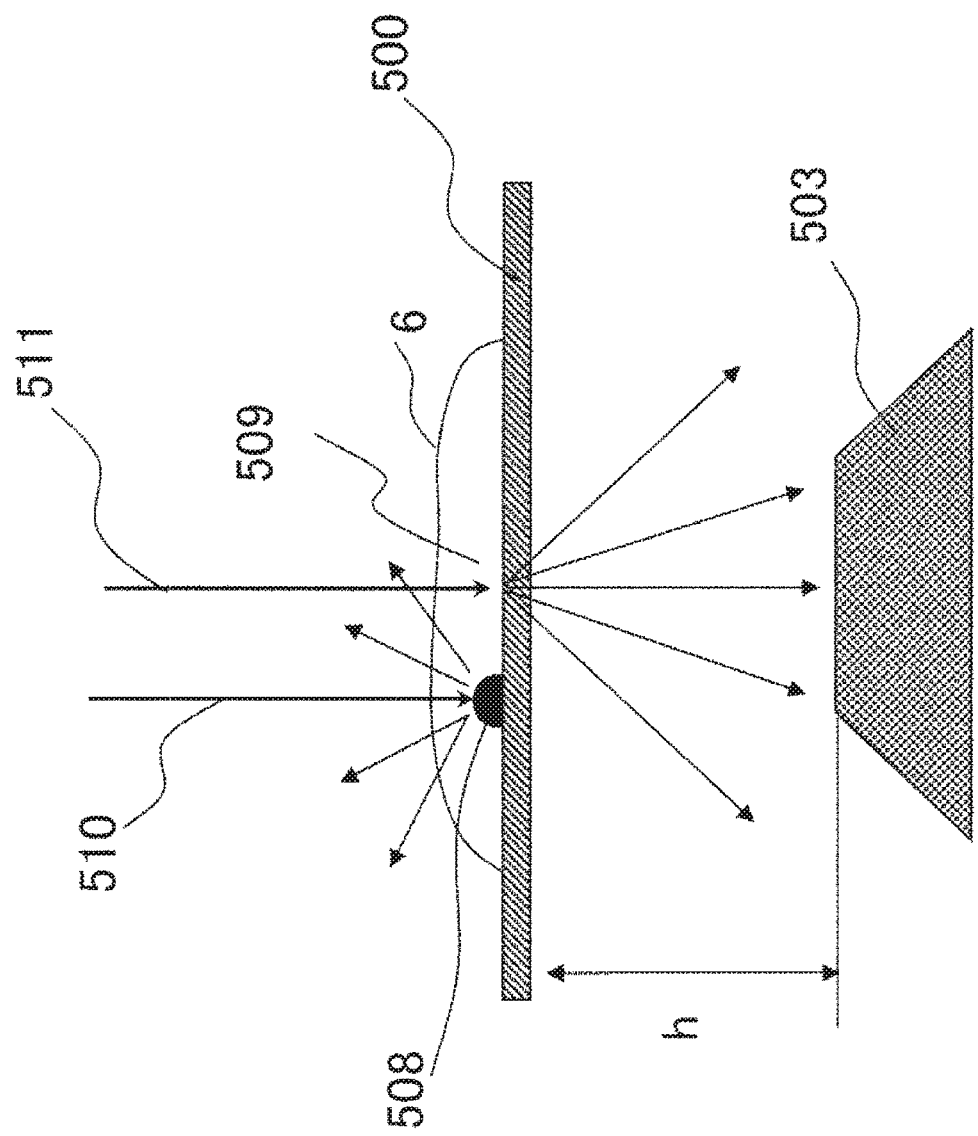

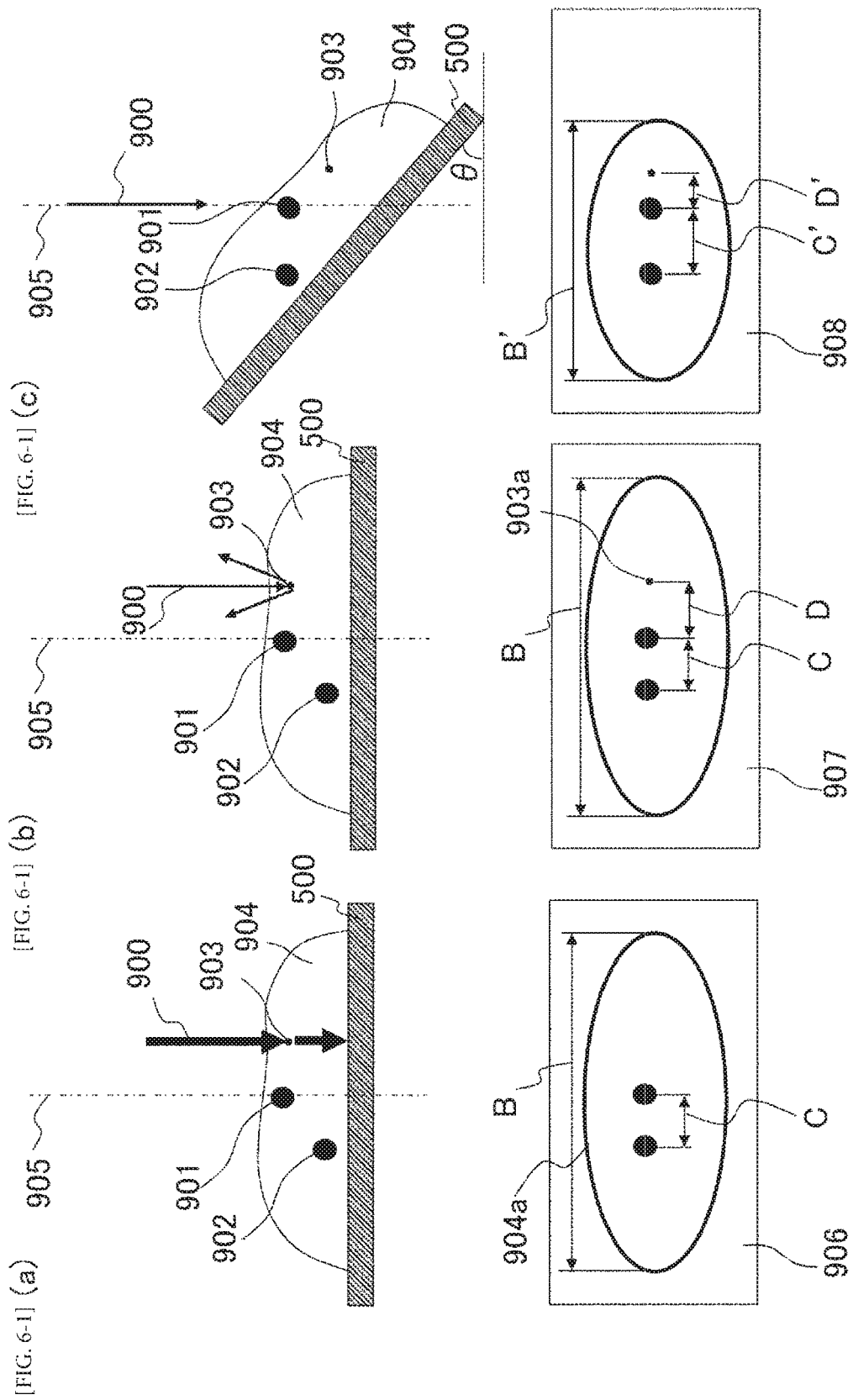

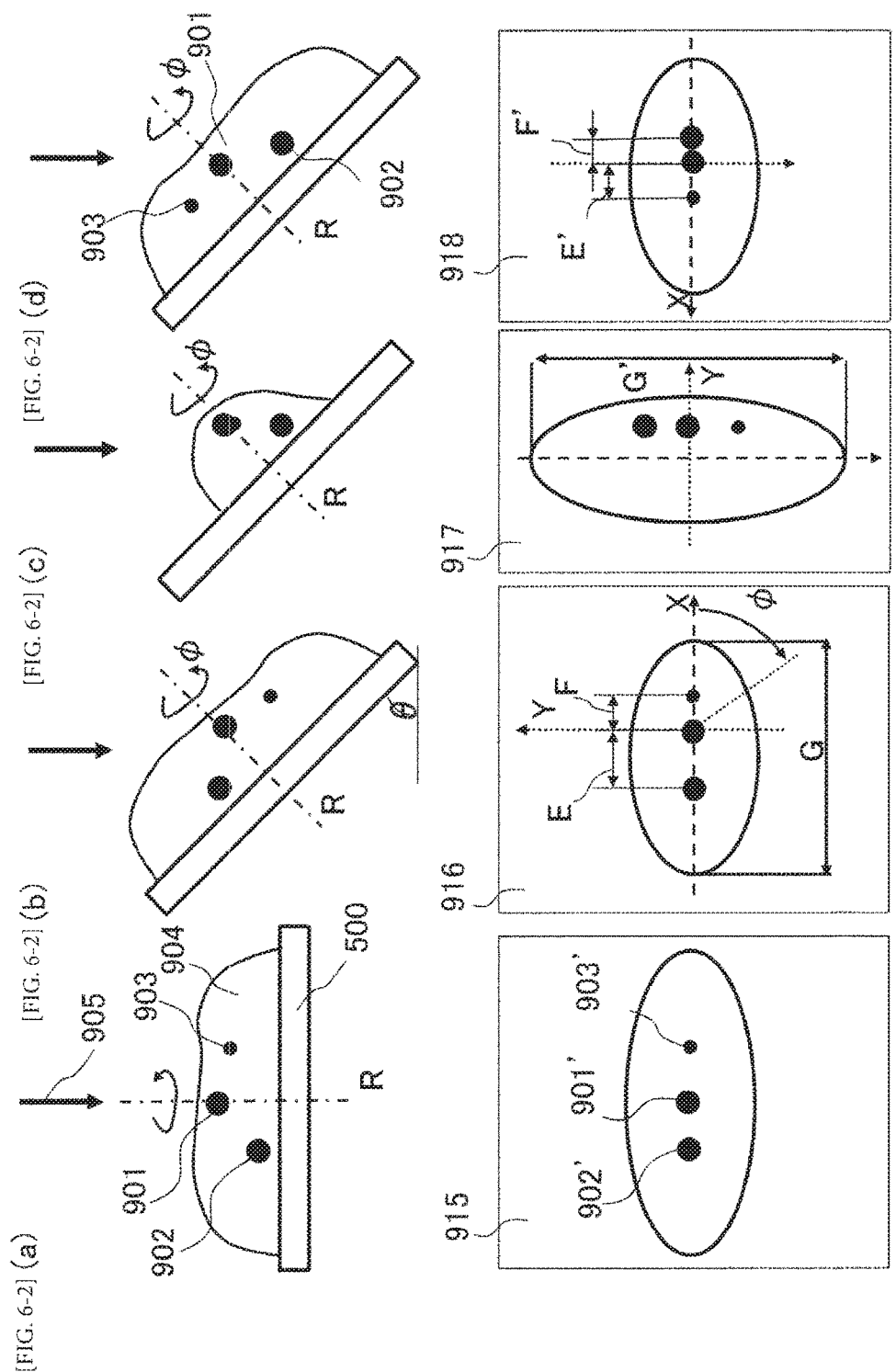

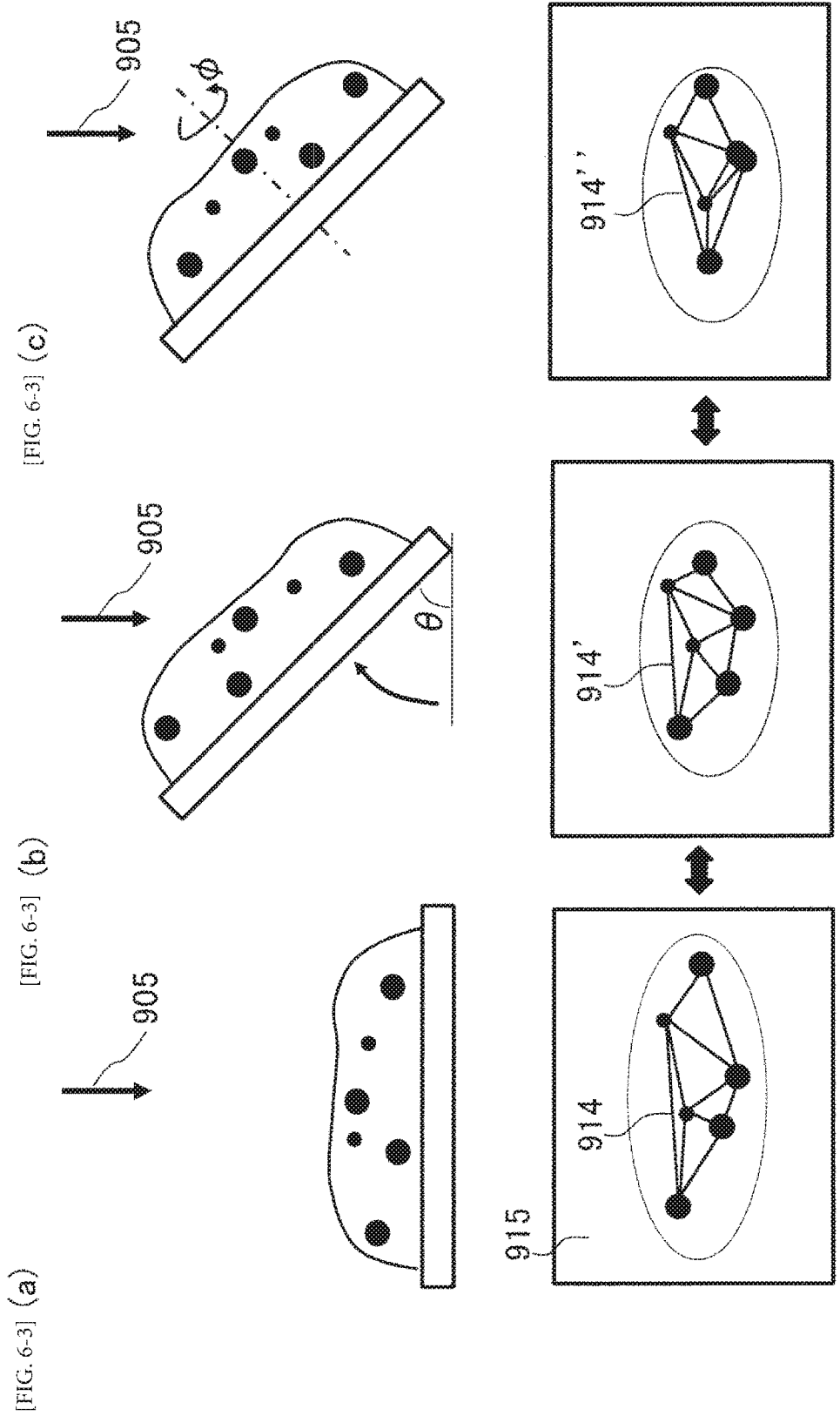

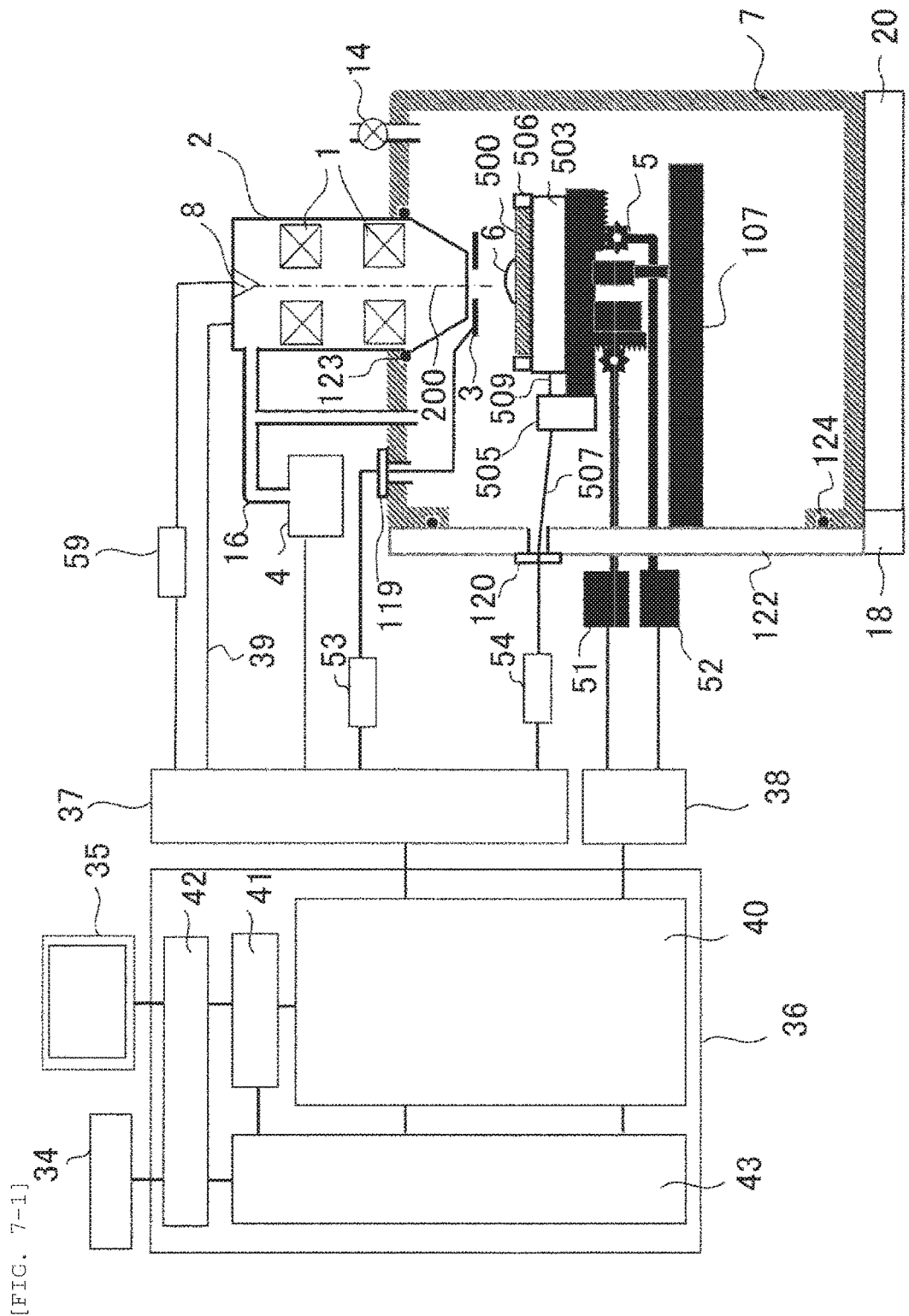
[FIG. 7-1]

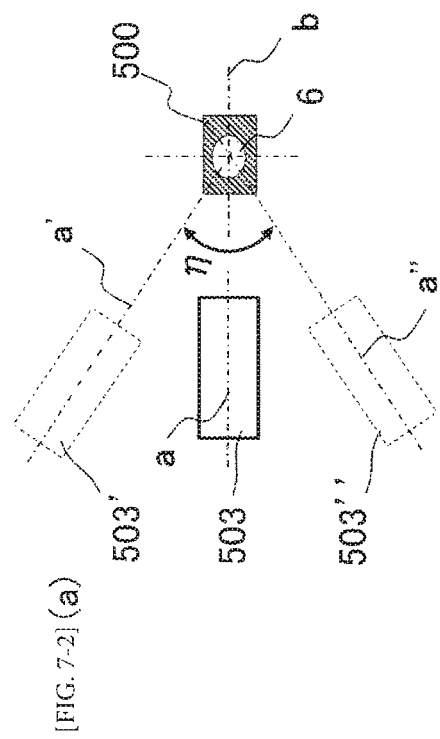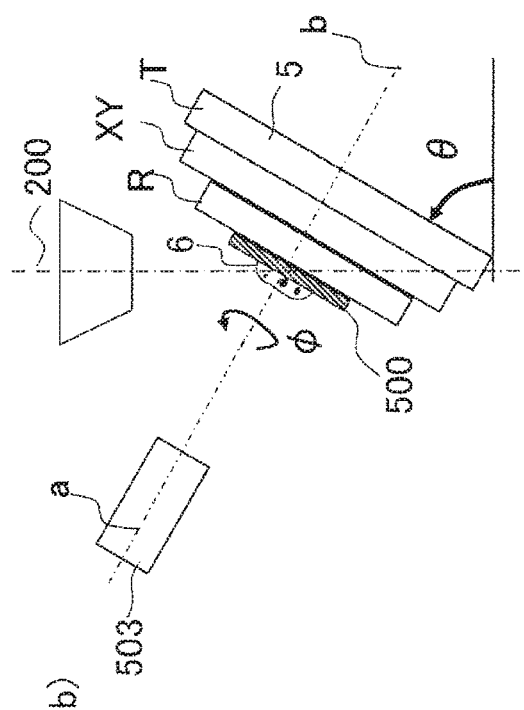
[FIG. 7-2] (a)
[FIG. 7-2] (b)

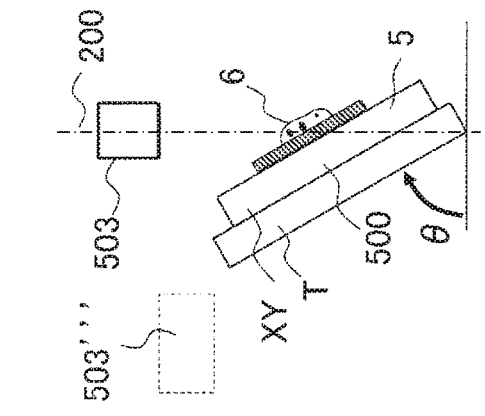
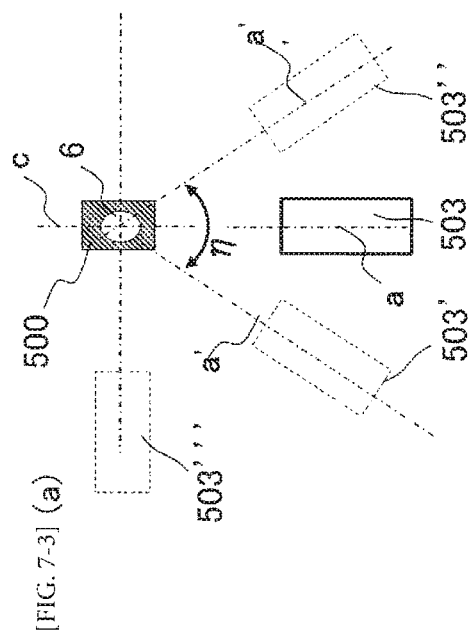
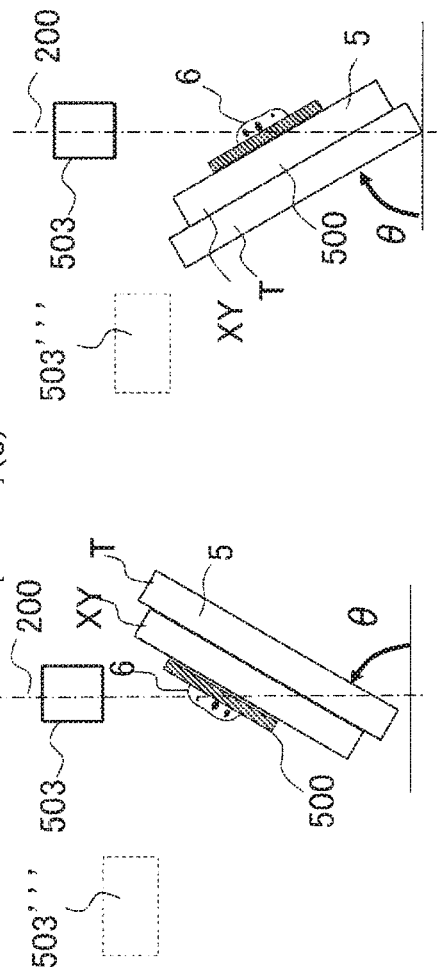

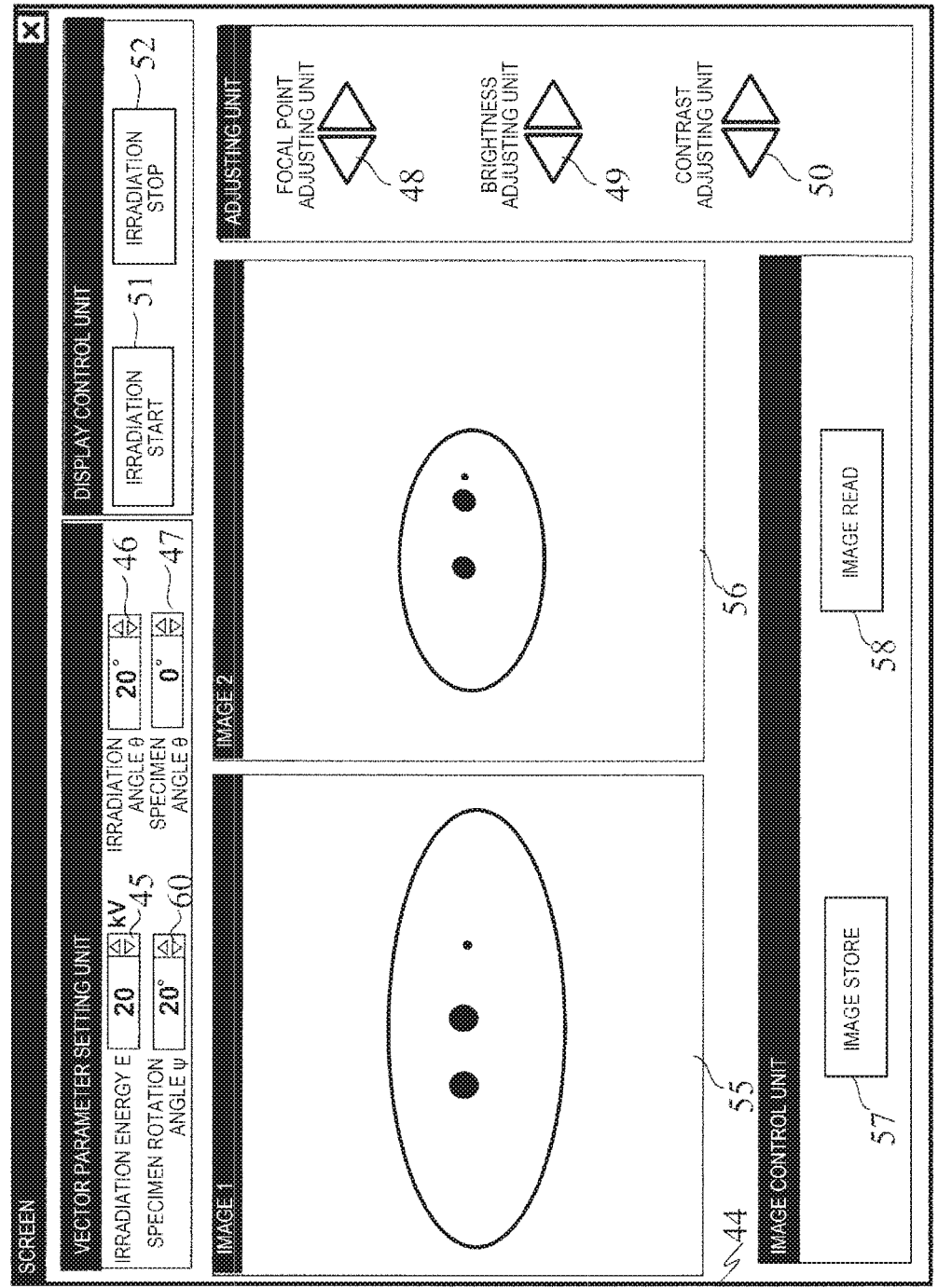

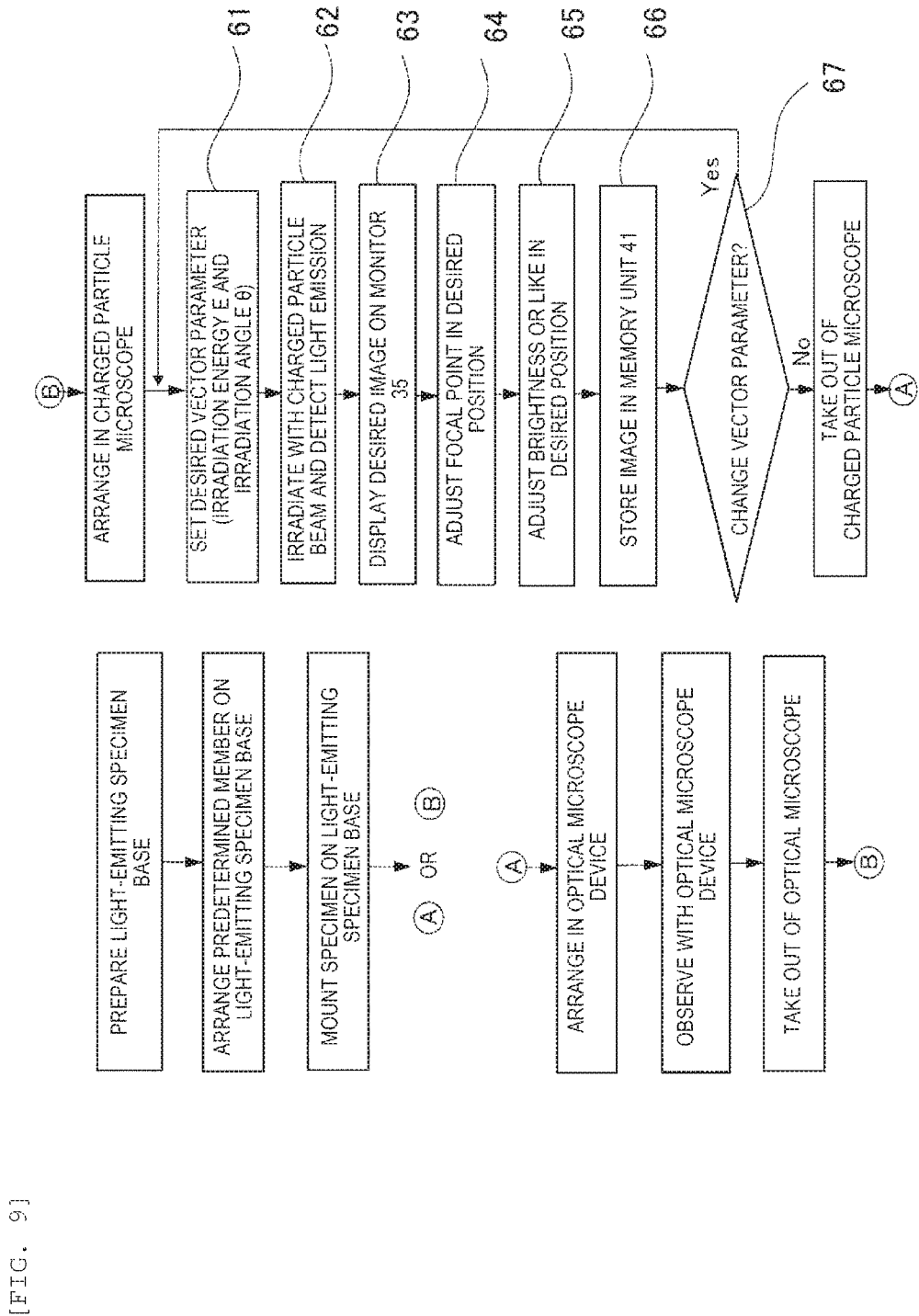
[FIG. 9]

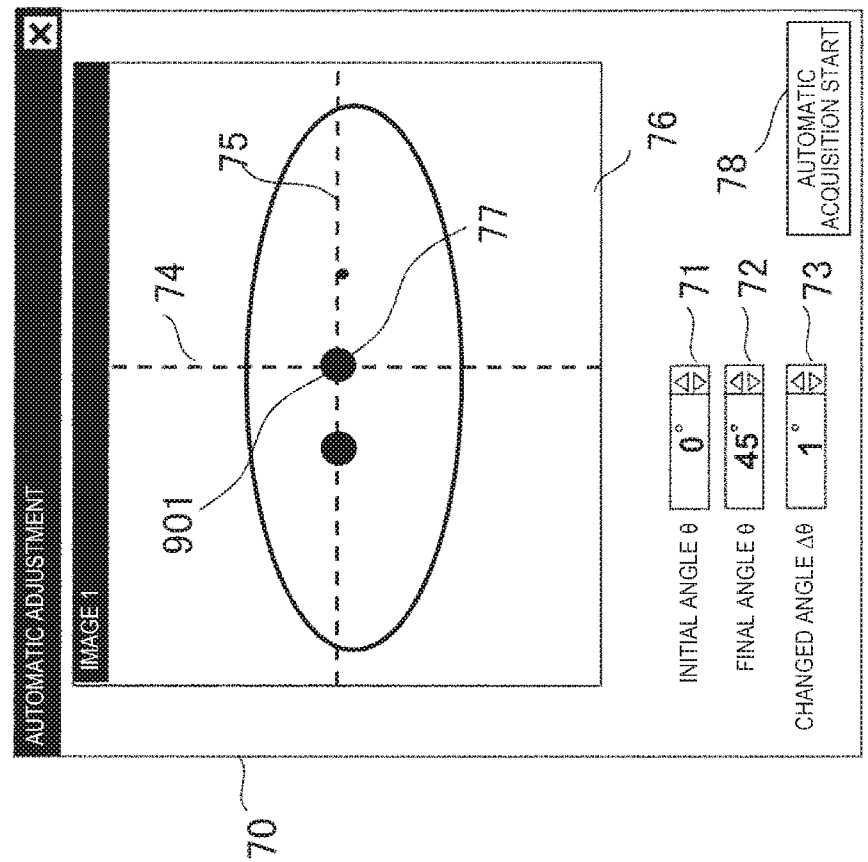
[FIG. 10]

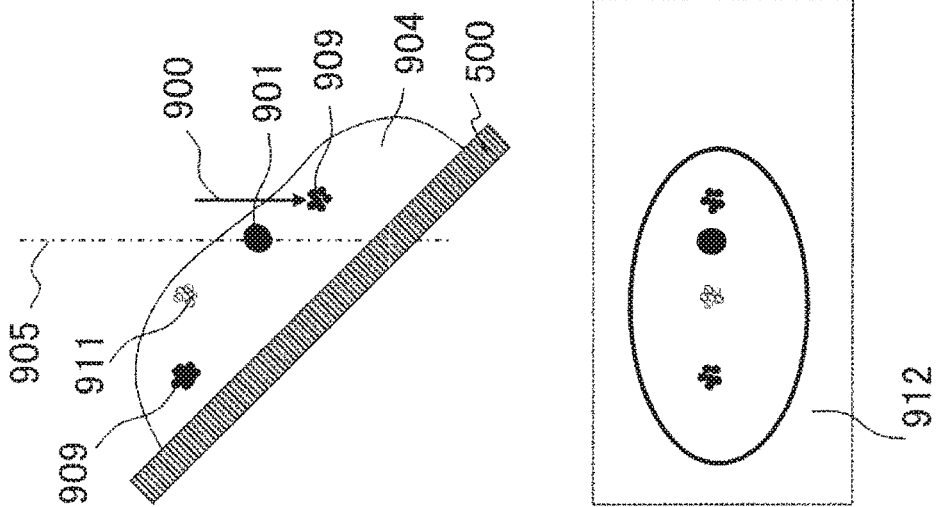
[FIG. 11] (a)
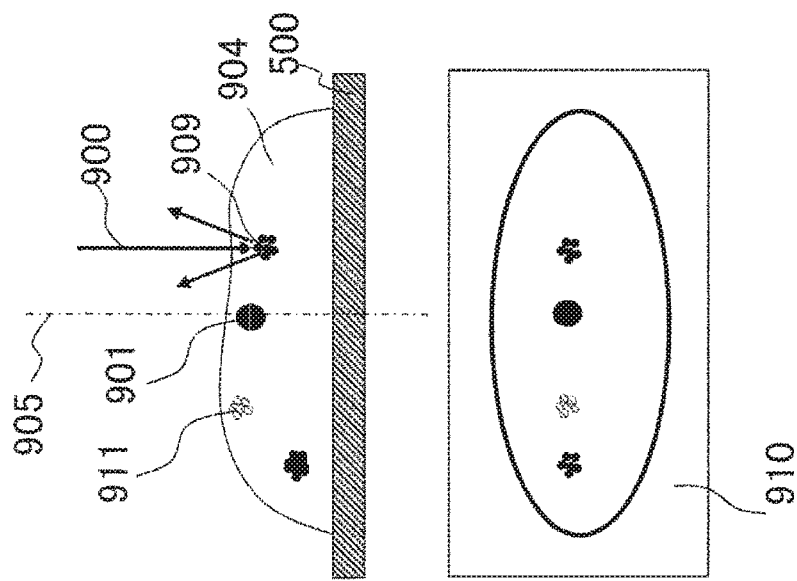
[FIG. 11] (b)

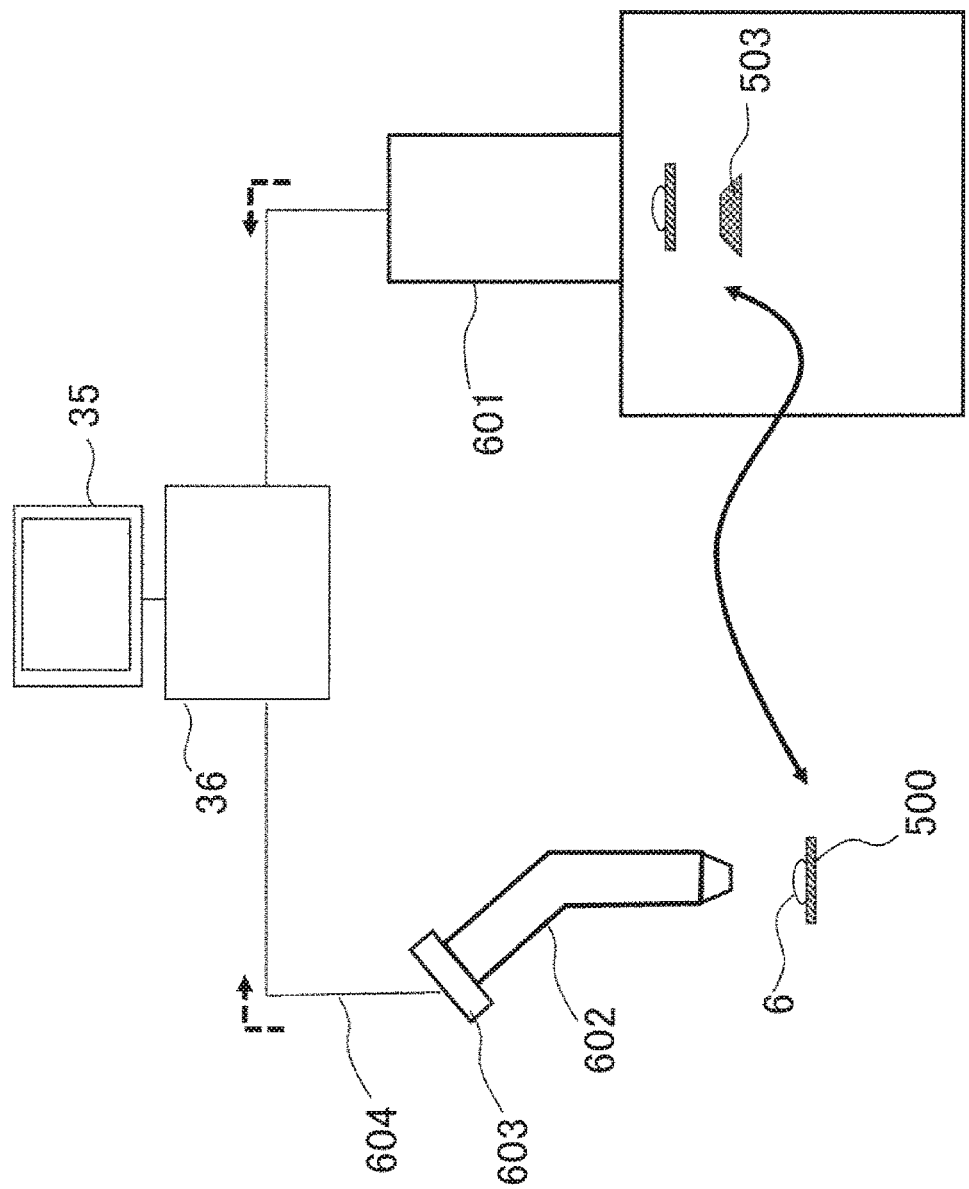
[FIG. 12]

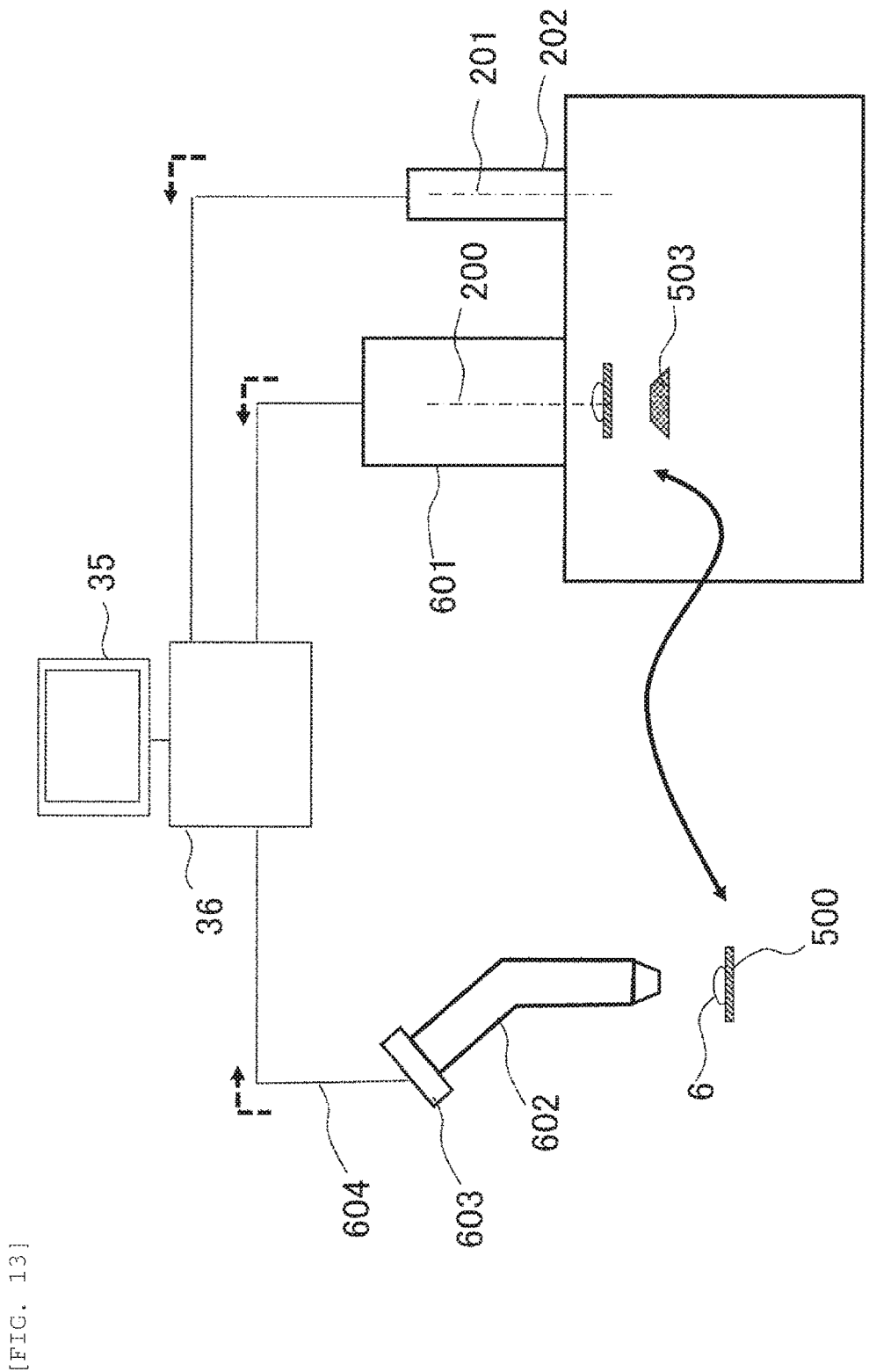
[FIG. 13]

[FIG. 14]
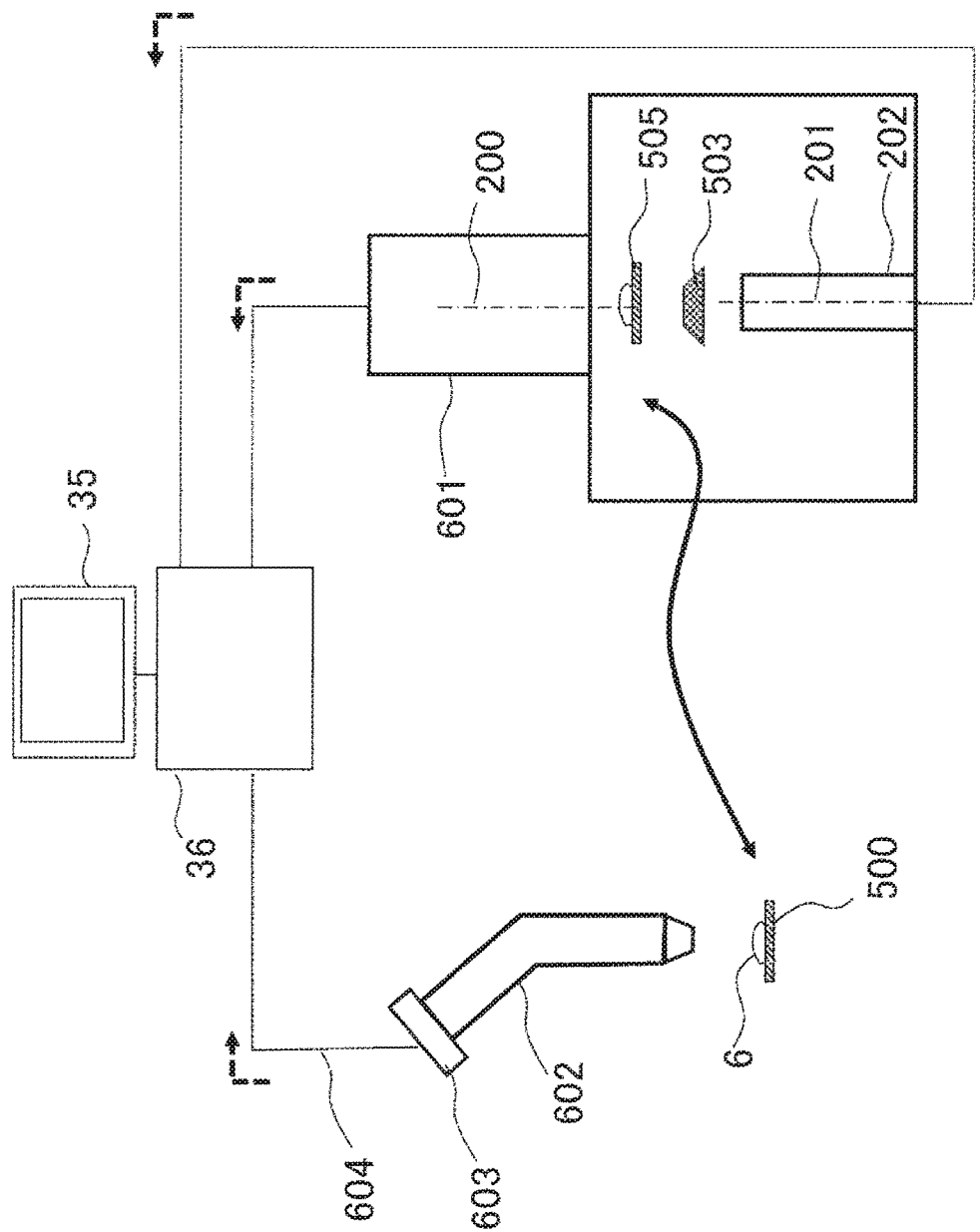

[FIG. 15]
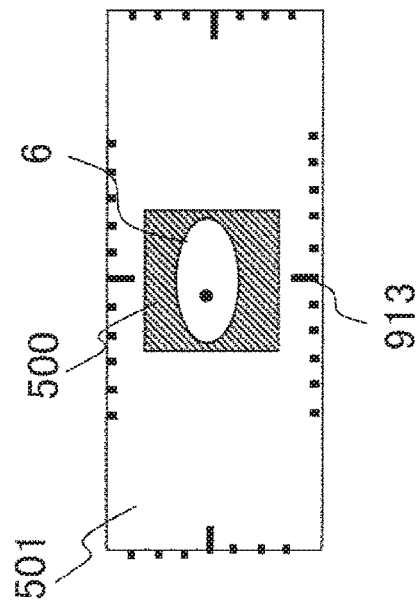
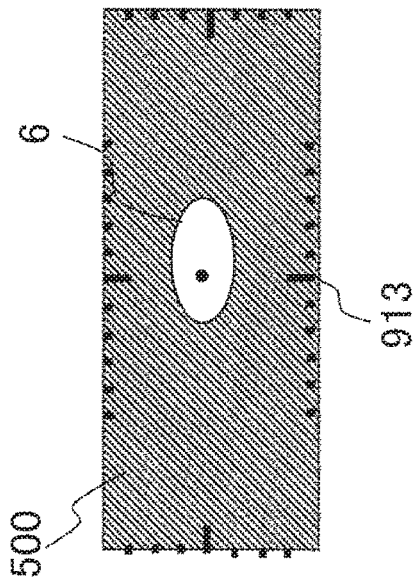

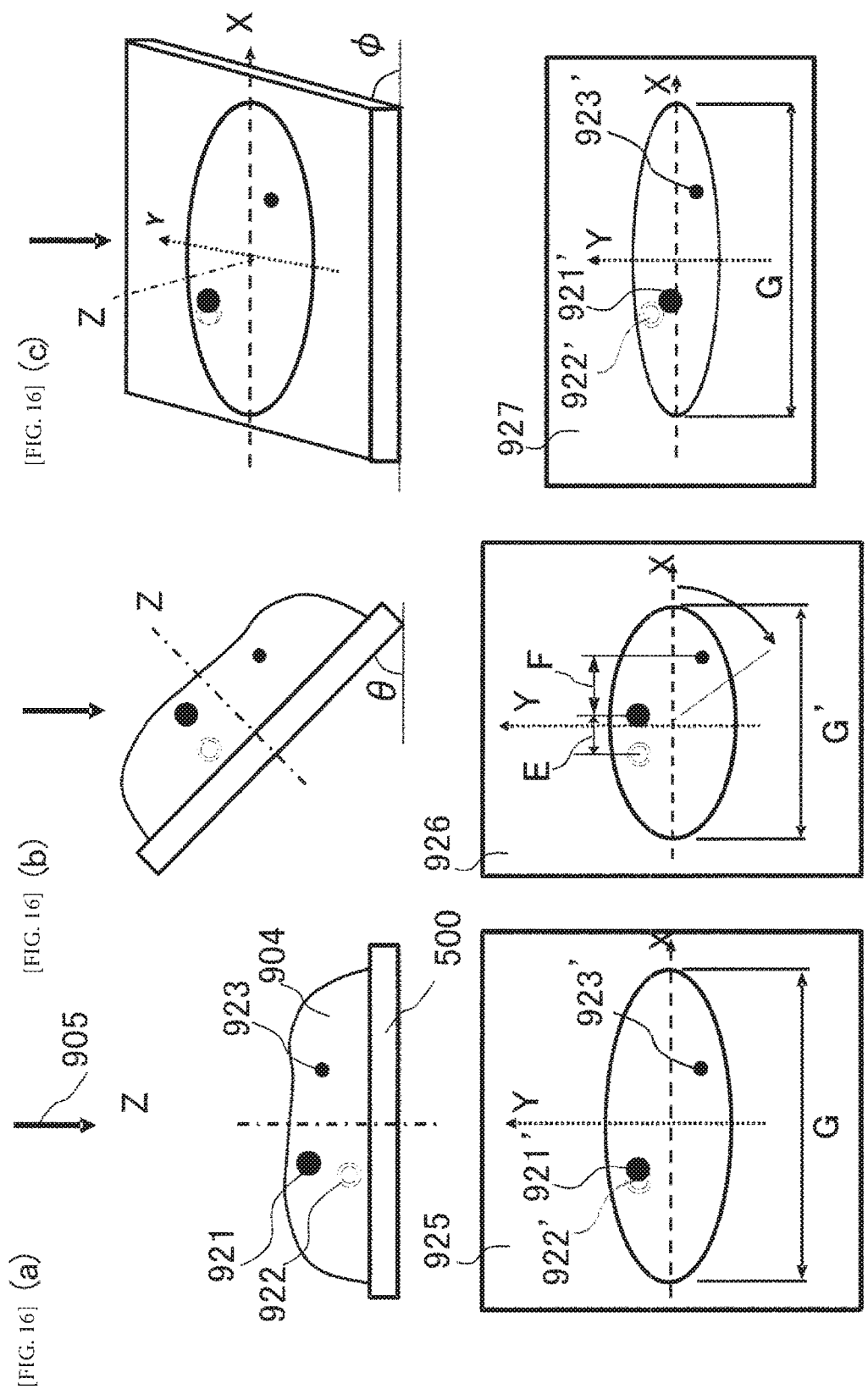

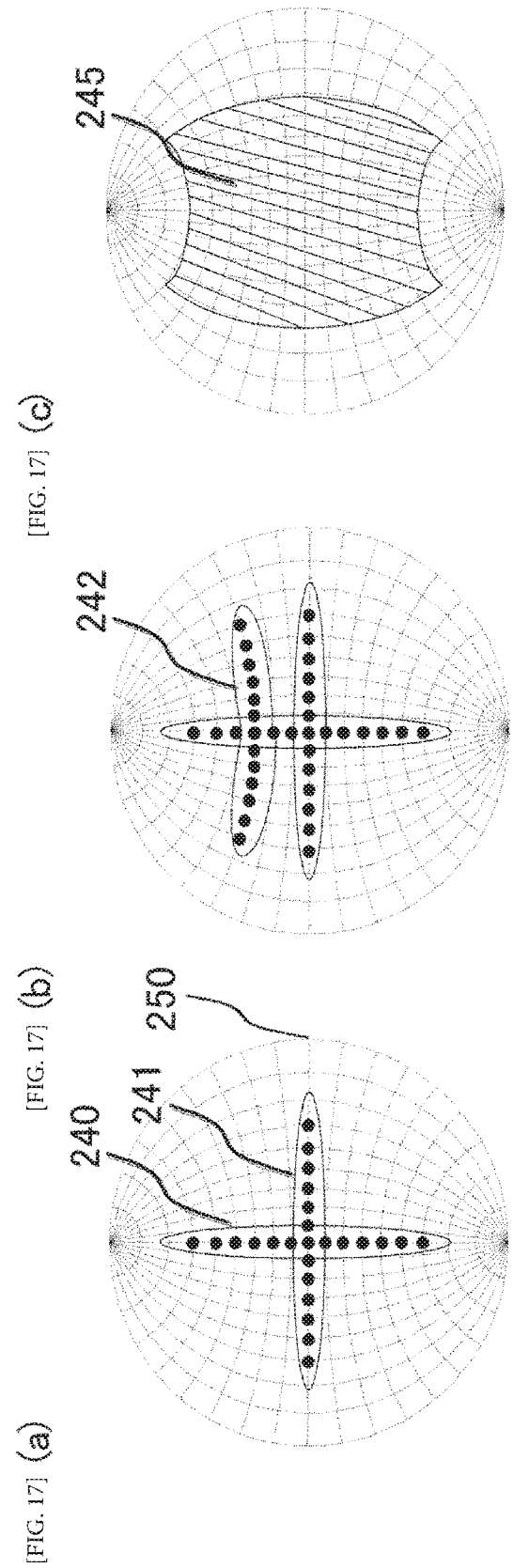

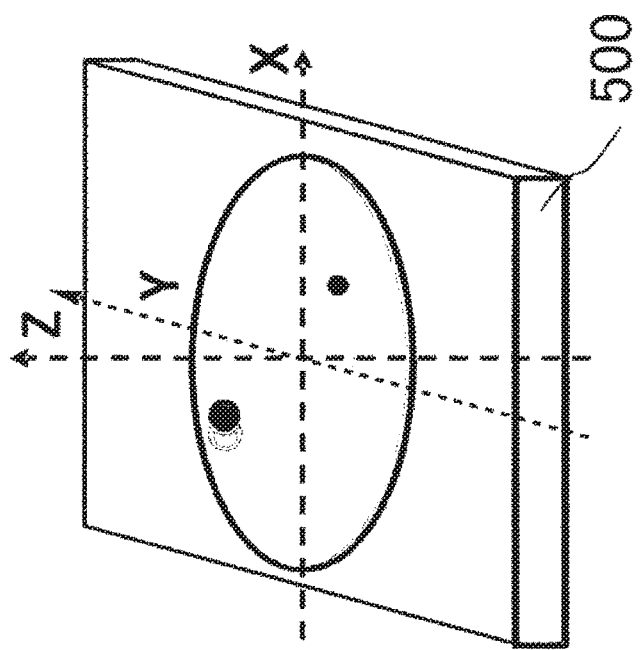
[FIG. 18]

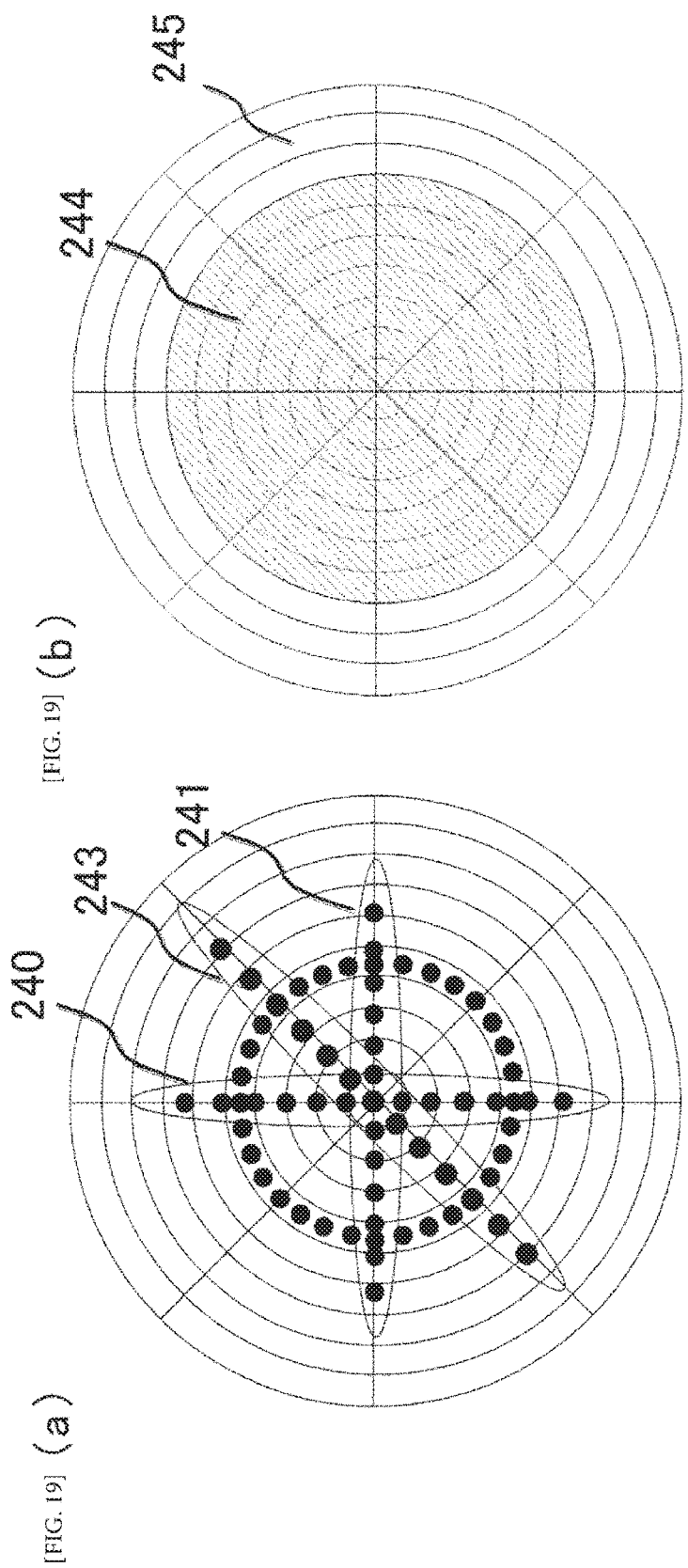

[FIG. 20]
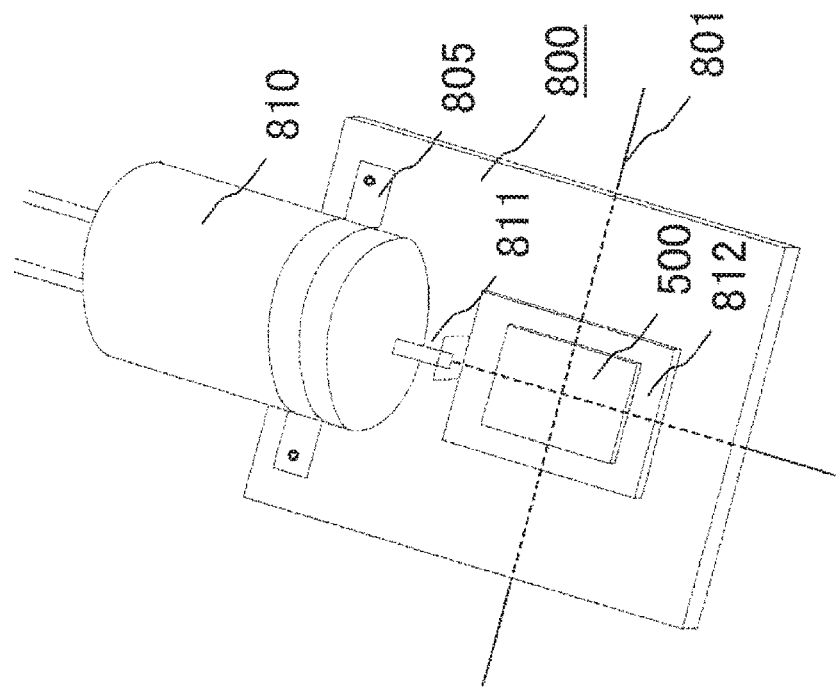

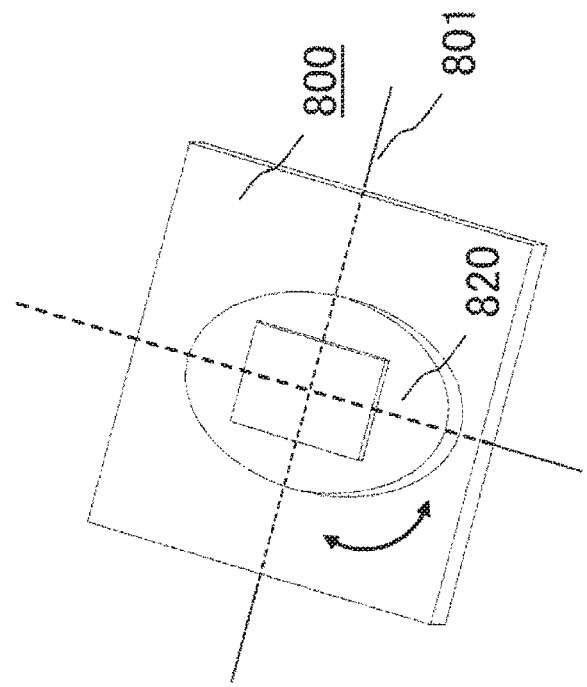
[FIG. 21]

[FIG. 22]
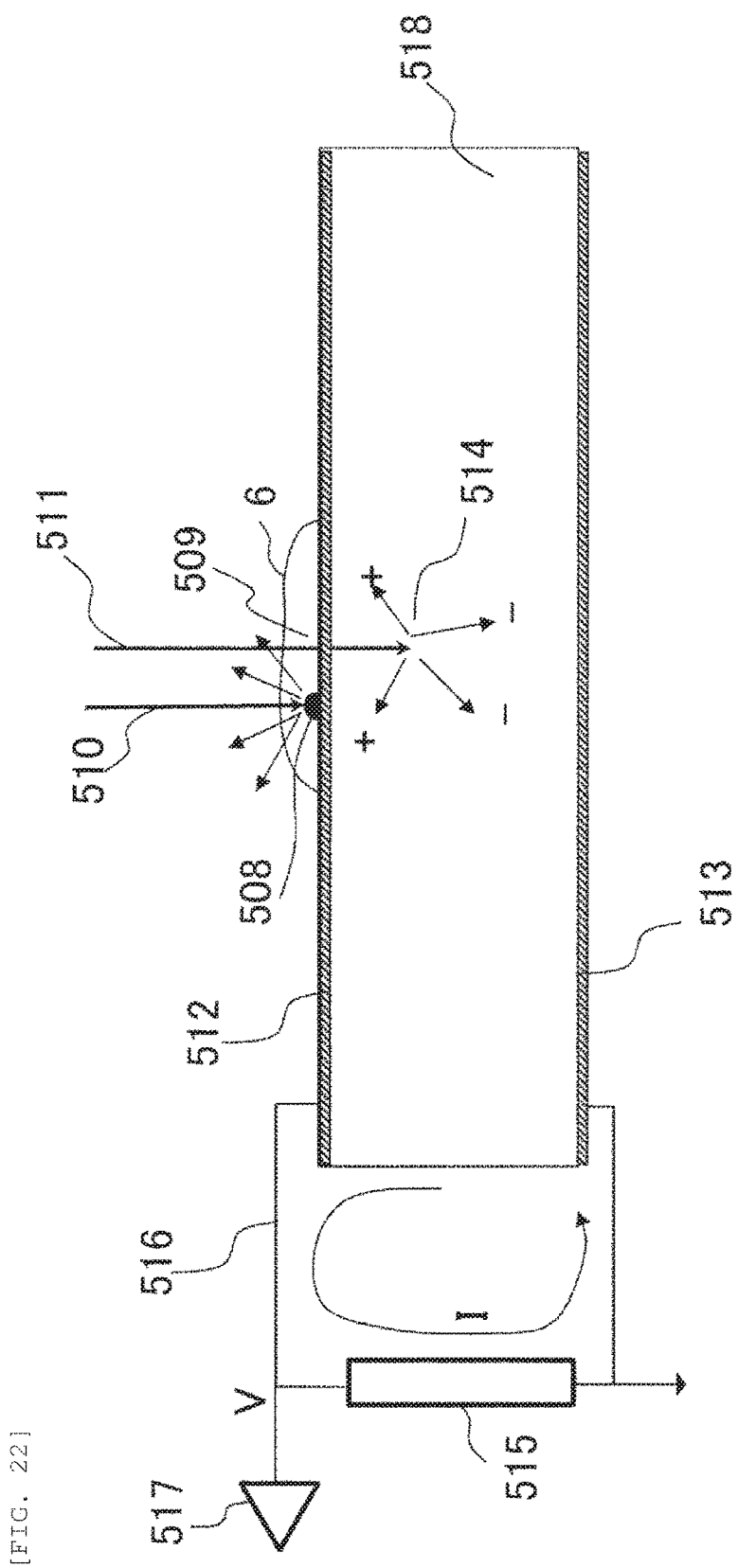

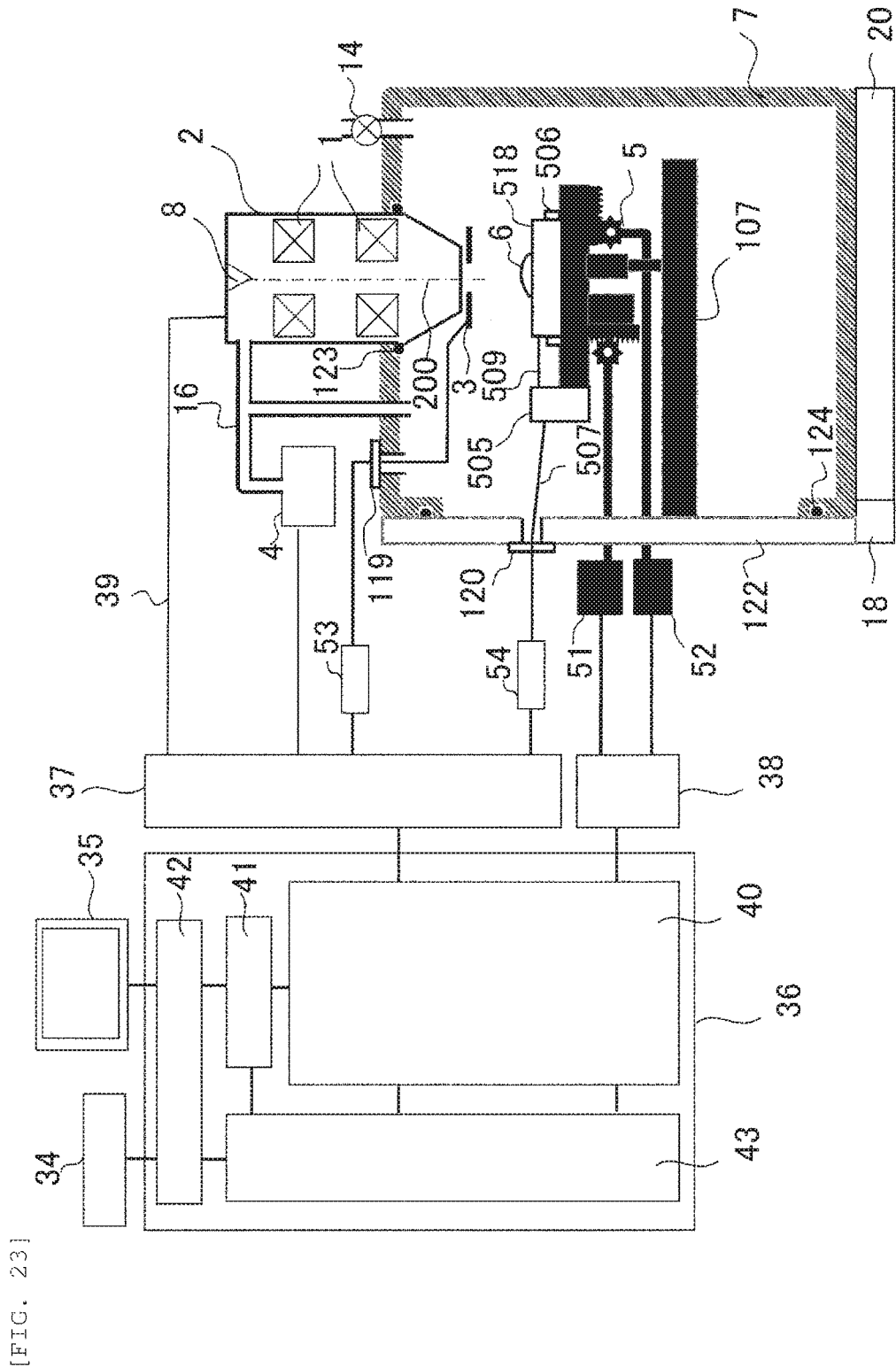
[FIG. 23]

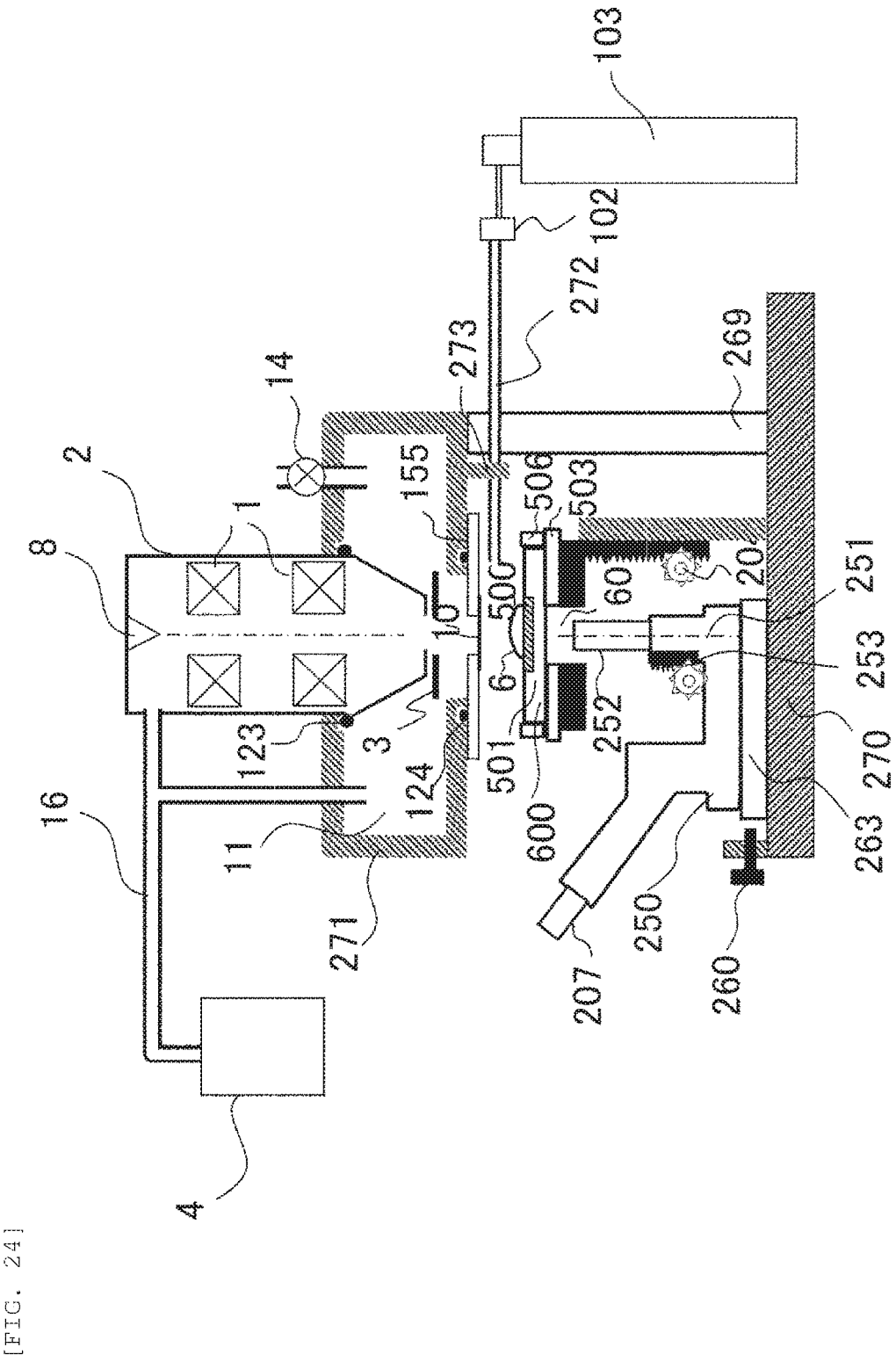
[FIG. 24]

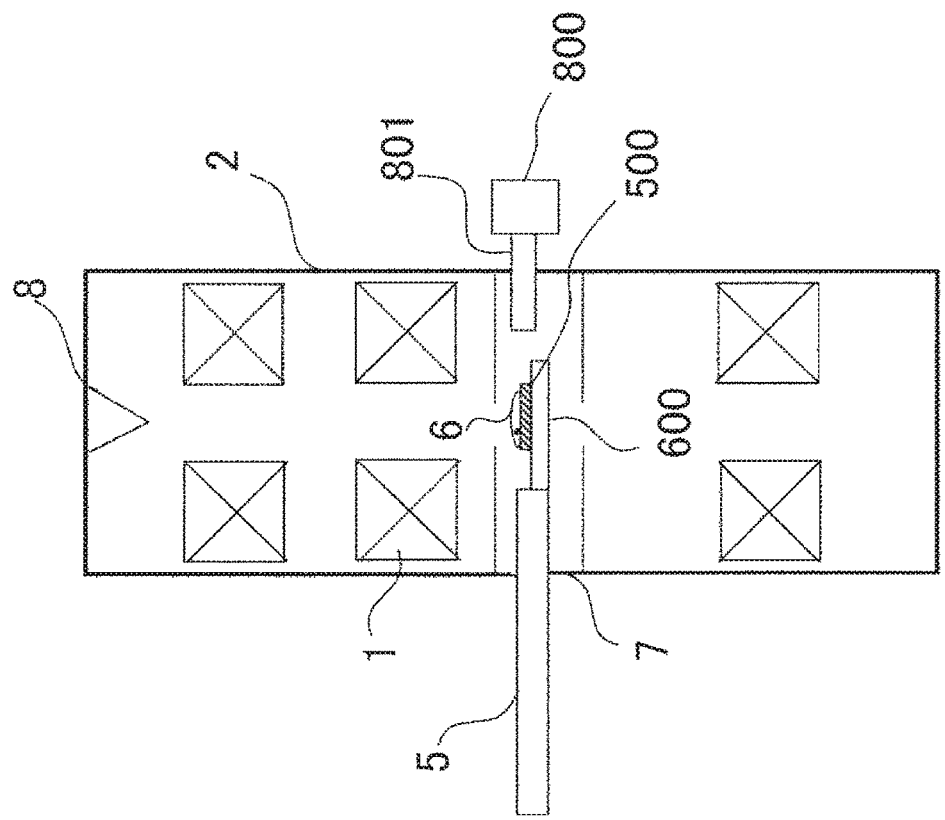
[FIG. 25]

CHARGED PARTICLE BEAM DEVICE

TECHNICAL FIELD

The present invention relates to a charged particle beam device and a specimen observation method capable of observing the inside of a specimen by irradiation with a charged particle beam.

BACKGROUND ART

A scanning transmission electron microscope (STEM), a transmission electron microscope (TEM), or the like is used to observe the internal structure of an object in a minute region of the object. As a general observation method for observing the inside of a specimen with use of such an electronic microscope, known is arranging, on a mesh specimen base that includes multiple holes, a specimen that is thinly sliced to the extent allowing transmission of an electronic beam and acquiring a transmitted electron beam at a detector that is arranged on the opposite side of a specimen surface from an electron source side. Furthermore, as a method for three-dimensionally observing the internal structure of an object, a method for acquiring transmission electron microscope images in various azimuths by inclining a specimen has recently drawn attention in the field of material, medical science, and biology. In PTL 1, suggested is a method for finding three-dimensional positional arrangement by inclining a specimen.

The internal structure of an object can be observed with not only the electronic microscope but also an optical microscope. Using the optical microscope allows acquisition of color information that cannot be acquired with the electronic microscope. As a specimen preparation method for optical microscopic observation, widely used is, for example, a method of placing a specimen thin enough for transmission of light or thinly applying a liquid-state specimen on a flat base such as a slide glass and observing the specimen.

CITATION LIST

Patent Literature

PTL 1: JP-A-4-337236 (U.S. Pat. No. 5,278,408)

SUMMARY OF INVENTION

Technical Problem

The optical microscope has a small depth of focus. Thus, an optical microscope image is an image that has information of only a specific depth or thickness of the specimen. Thus, even if the slide glass or the like is inclined, the three-dimensional internal structure of the specimen cannot be observed. Meanwhile, the electronic microscope has a great depth of focus compared with the optical microscope. Thus, information is superimposed in the depth direction in one image. Therefore, observing a three-dimensional structure inside the specimen with use of the electronic microscope requires accurate specification of the size and the density of a structure and the position thereof in a three-dimensional direction inside the specimen.

Furthermore, in the case of observing, with the electronic microscope, the three-dimensional internal structure of the specimen that is observed with the optical microscope, the specimen that is observed with the optical microscope is required to be introduced into an electronic microscope device capable of three-dimensional structure observation as in PTL 1. However, the specimen mounted on the slide glass cannot be put into a TEM or STEM device as in the known literature. Thus, three-dimensional internal structure observation of a location that is observed with the optical microscope is difficult to perform with the electronic microscope. Although this can be realized by, for example, solidifying, with a resin, the specimen observed with the optical microscope on the flat base such as a slide glass, peeling the specimen from the flat base and then thinly slicing the specimen with a microtome or the like, and arranging the specimen on a mesh that includes multiple holes, this work is a very complicated work of replacement of the specimen.

The invention is conceived in view of such problems, and an object thereof is to provide a charged particle beam device and a specimen observation method that can accurately specify a three-dimensional positional relationship or a density distribution of a specimen internal structure with a transmitted charged particle beam image.

Solution to Problem

In order to resolve the above problems, a charged particle beam device in the invention includes a charged particle optical column that irradiates a specimen held in a specimen base with a primary charged particle beam, a specimen base rotating unit that is capable of rotating the specimen base in a state of an angle formed by a surface of the specimen base and an optical axis of the primary charged particle beam being inclined to a non-perpendicular angle, and a control unit that controls a rotation angle of the specimen base rotating unit, in which the specimen base is configured to include a detecting element that detects a charged particle scattered or transmitted inside the specimen, and transmitted charged particle images of the specimen corresponding to each angle is acquired by irradiating the specimen with the primary charged particle beam in a state of the specimen base rotating unit being rotated at a plurality of different angles.

In addition, another charged particle beam device in the invention includes a charged particle optical column that irradiates a specimen held in a specimen base with a primary charged particle beam, a specimen stage in which the specimen base is arranged in an attachably detachable manner, and an angle control unit that controls a relative angle between the primary charged particle beam and the specimen with a first axis and a second axis different from the first axis, in which the specimen base is configured to include a detector that detects a charged particle scattered or transmitted inside the specimen, and transmitted charged particle images of the specimen corresponding to each relative angle are acquired by performing irradiation with the primary charged particle beam at a plurality of the different relative angles in the first axis and in the second axis.

In addition, still another charged particle beam device in the invention includes a charged particle optical column that irradiates a specimen held in a specimen base with a primary charged particle beam, a specimen stage in which the specimen base is arranged in an attachably detachable manner, a specimen base inclining unit that inclines an angle formed by a surface of the specimen base and an optical axis of the primary charged particle beam to a non-perpendicular angle with an inclination axis different from an inclination axis of the specimen stage, and a control unit that controls an inclination angle of the specimen base inclining unit, in which the specimen base is configured to include a detecting unit that detects a charged particle scattered or transmitted inside the specimen, and transmitted charged particle images of the specimen corresponding to each relative angle are acquired by inclining the specimen base at a plurality of the different relative angles with the inclination axis different from the specimen stage and by irradiating the specimen with the primary charged particle beam.

Advantageous Effects of Invention

According to the invention, a three-dimensional positional relationship or a density distribution of a specimen internal structure can be accurately specified with a transmitted charged particle beam image.

Particularly, using a specimen base that allows detection of a transmitted charged particle beam allows three-dimensional internal structure observation of a specimen observed with an optical microscope to be simply performed with a charged particle microscope device.

Problems, configurations, and effects other than the above will become apparent from description of embodiments below.

BRIEF DESCRIPTION OF DRAWINGS

FIG. 1 is a schematic descriptive diagram of optical microscopic observation and charged particle beam microscopic observation.

FIG. 2 is a detailed diagram of a specimen base that includes a detecting element.

FIGS. 3(a) and 3(b) are detailed diagrams of the specimen base that includes the detecting element.

FIGS. 4(a) and 4(b) are detailed diagrams of the specimen base that includes the detecting element.

FIG. 5 is a descriptive diagram of a method for detecting a transmitted charged particle with the detecting element.

FIGS. 6-1(a) to 6-1(c) are descriptive diagrams of a method for detecting a transmitted charged particle with the detecting element.

FIGS. 6-2(a) to 6-2(d) are descriptive diagrams of a method for detecting a transmitted charged particle with the detecting element.

FIGS. 6-3(a) to 6-3(c) are descriptive diagrams of a method for detecting a transmitted charged particle with the detecting element.

FIG. 7-1 is a description of a device in Embodiment 1.

FIGS. 7-2(a) and 7-2(b) are descriptions of the device in Embodiment 1.

FIGS. 7-3(a) to 7-3(c) are descriptions of the device in Embodiment 1.

FIG. 8 is a descriptive diagram of an operating screen.

FIG. 9 is a descriptive diagram of an observation method in Embodiment 1.

FIG. 10 is a descriptive diagram of the operating screen.

FIGS. 11(a) and 11(b) are descriptive diagrams of a method for detecting a transmitted charged particle with the detecting element.

FIG. 12 is a schematic descriptive diagram of optical microscopic observation and charged particle beam microscopic observation.

FIG. 13 is a schematic descriptive diagram of optical microscopic observation and charged particle beam microscopic observation.

FIG. 14 is a schematic descriptive diagram of optical microscopic observation and charged particle beam microscopic observation.

FIG. 15 is a detailed diagram of the specimen base that includes the detecting element.

FIGS. 16(a) to 16(c) are descriptive diagrams of a method for detecting a transmitted charged particle with the detecting element.

FIGS. 17(a) to 17(c) are diagrams of a stereographic projection of the relative angle between a specimen and a charged particle beam.

FIG. 18 is a diagram illustrating a coordinate relationship between the specimen and inclination or rotation.

FIGS. 19(a) and 19(b) are diagrams of a stereographic projection of the relative angle between the specimen and the charged particle beam.

FIG. 20 is a diagram representing inclination at a stage and inclination at a motor.

FIG. 21 is a diagram representing inclination at the stage and rotation at a rotation base.

FIG. 22 is a descriptive diagram of a detecting element in Embodiment 2.

FIG. 23 is a descriptive diagram of a device in Embodiment 2.

FIG. 24 is a descriptive diagram of a device in Embodiment 3.

FIG. 25 is a descriptive diagram of the device in Embodiment 3.

DESCRIPTION OF EMBODIMENTS

The present application incorporates the content of PCT/JP2014/056392 that constitutes a part of the present specification. The above application is considered not to be known at the time of application of the present application. Hereinafter, each embodiment will be described by using the drawings.

Hereinafter, details of a specimen base and a charged particle beam device to which the specimen base is applied in the invention will be described. These are merely one example of the invention, and the invention is not limited to the embodiments described below. The invention can be applied to a device that observes a specimen with charged particle beam irradiation, such as a scanning electron microscope, a scanning ion microscope, a scanning transmission electron microscope, or a transmission electron microscope, to a combined device of the microscope and a specimen working device, or to an analysis or test device to which the microscope is applied. The specimen base and the charged particle beam device in which the specimen base is mounted in the invention constitute an observation system that allows observation of a transmitted charged particle beam image.

The "specimen base" in the present specification means a unit that can be detached along with a specimen from the charged particle beam device in a state of the specimen being mounted on the unit. Specifically, as described below, the "specimen base" unit may have a detecting element and a base or may be formed to have only a detecting element.

Embodiment 1

<Summary>

First, a summary of the specimen base used in the present embodiment will be described. While a three-dimensional internal structure observation method described below can be used for a general electron microscope specimen base in the related art, usability of the method is further improved by using the specimen base described next.

The present embodiment will describe a charged particle microscope and an observation system that generate a transmitted charged particle beam image by converting charged particle beam transmitted or scattered inside the specimen into light and detecting the light. More specifically, at least a part of the specimen base on which the specimen is mounted is formed as a light-emitting member that emits light by being irradiated with a charged particle beam. Irradiation of the light-emitting member with a charged particle beam that is transmitted or scattered by the specimen on the light-emitting member generates light, and the light is detected in a detector included in the charged particle microscope to generate a transmitted charged particle beam image. That is, the charged particle beam that is transmitted by the specimen is not directly detected and is detected after being converted into light in the present embodiment. As described in detail below, the light-emitting member that converts the charged particle beam into light does not require externally connected interconnects such as a power cable and a signal line. Thus, the same specimen base can be used to perform observation in the charged particle beam microscope and in another device, and a very effortful work of detaching an electric interconnect at the time of moving the specimen between devices is not required. In addition, the light-emitting member or the specimen base having the light-emitting member can be simply attached to or detached from the device. Thus, for any specimen, the specimen can be simply set on the specimen base. Particularly, this is very effective in the case of observing a cultured cell or the like that requires culturing of the specimen on the specimen base for microscopic observation.

Furthermore, as illustrated in FIG. 1, if the specimen base of the present embodiment is used, observation with the charged particle beam microscope and observation with another device such as an optical microscope can be performed with the same specimen base. FIG. 1 illustrates a specimen base that includes a detecting element 500 (may be referred to as a light-emitting member) capable of light emission by converting or amplifying the charged particle beam into light, a charged particle beam microscope 601, and an optical microscope 602 in the present embodiment. A specimen 6 can be mounted on the detecting element 500 of the specimen base directly or through a predetermined member described later. As described later, the charged particle beam microscope 601 includes an optical detector 503 in order to convert and amplify light from the detecting element 500 into an electrical signal. With this configuration, a transmitted charged particle microscopic image can be acquired by converting, into light, a "charged particle transmission signal" transmitted or scattered inside the specimen after irradiation of the specimen 6 with the charged particle beam generated in the charged particle beam microscope and by detecting the light in the detecting element forming a part of the specimen base. In addition, since the present specimen base is a common specimen base used in common in the charged particle beam microscope and in the optical microscope, moving the same specimen base between microscopes as illustrated by an arrow in the drawing and performing observation allows charged particle beam observation and optical observation with the specimen arranged on one specimen base without duplicating the specimen for each microscopic observation or moving the specimen.

In the present embodiment, the detecting element forming apart of the specimen base may be made as a transparent member. Hereinafter, in the present specification, the meaning of "transparent" means allowing passage of visible light, ultraviolet light, or infrared light in a specific wavelength region or allowing passage of visible light, ultraviolet light, or infrared light in all wavelength regions. Ultraviolet light has a wavelength region of approximately 10 to 400 nm. Visible light has a wavelength region of approximately 380 nm to 750 nm. Infrared light has a wavelength region of approximately 700 nm to 1 mm (=1,000 µm). For example, if transparency is seen even with a few mixed colors, this means allowing passage of visible light in a specific wavelength region. If colorless transparency is seen, this means allowing passage of visible light in all wavelength regions. "Allowing passage" indicates passage of light of intensity with which optical microscopic observation can be performed with light in the wavelength region (desirably, for example, a transmittance of greater than or equal to 50%). In addition, the specific wavelength region is a wavelength region that includes a wavelength region used in observation with at least the optical microscope. Thus, the detecting element can be used in a general optical microscope (transmission optical microscope) that can detect, from the other surface side of the specimen base, an "optical transmission signal" acquired by light from one surface side of the specimen base of the present embodiment being transmitted by the specimen. Any microscope using light such as a biological microscope, a stereoscopic microscope, an inverted microscope, a metallographic microscope, a fluorescence microscope, or a laser microscope may be used as the optical microscope. In addition, while the term "microscope" is used for description, the specimen base can be applied to general devices that acquire information by irradiating the specimen with light regardless of magnifications of images.

Furthermore, if the specimen base is used, three-dimensional internal structure observation of the specimen arranged on the common specimen base can be performed in the charged particle microscope device after optical microscopic observation. Thus, various types of information can be obtained from the same specimen on the same specimen base. Hereinafter, details of the specimen base, a specimen mounting method, an image acquisition principle, a device configuration, and the like will be described.

<Description of Specimen Base>

Details and the principle of the specimen base in the present embodiment will be described. The specimen base of the present embodiment is configured of the detecting element 500 that converts the charged particle beam into light. The specimen 6 is directly mounted on the detecting element 500 as in FIG. 2. While only one specimen 6 is mounted in the drawing, a plurality of specimens 6 may be arranged. The specimen 6 may be indirectly mounted through a member such as a film as described later. A base 501 (not illustrated) that is colorless and transparent or has a few mixed colors may be arranged under the specimen base 500. Transparent glass, transparent plastic, transparent crystal, or the like is used as the base 501. In the case of desiring observation with a fluorescence microscope or the like, plastic is favorable since plastic does not absorb fluorescence. The base 501 may not be included.

The detecting element 500 is an element that detects a charged particle beam arriving at an energy of, for example, a few keV to a few tens of keV and emits light such as visible light, ultraviolet light, or infrared light if being irradiated with the charged particle beam. In the case of using the detecting element in the specimen base of the present embodiment, the detecting element converts, into light, a charged particle that is transmitted or scattered inside the specimen mounted on the specimen base. The wavelength of emitted light is preferably a specific or any wavelength region of visible light, ultraviolet light, and infrared light. For example, a scintillator or a luminescent light-emitting material can be used as the detecting element. Examples of the scintillator include inorganic scintillator materials such as silicon nitride (SiN) and yttrium aluminum garnet (YAG) elements, yttrium aluminum perovskite (YAP) elements, bismuth germanium oxide (BGO) elements, gadolinium silicon oxide (GSO) elements, lutetium silicon oxide (LSO) elements, yttrium silicon oxide (YSO) elements, lutetium yttrium silicon oxide (LYSO) elements, and thallium-activated sodium iodide (NaI (Tl)) elements. Materials to which a plastic scintillator or an organic scintillator containing a material such as polyethylene terephthalate capable of emitting light or a liquid scintillator containing anthracene or the like is applied may also be used. The detecting element 500 may be any material provided that the detecting element 500 is an element capable of converting the charged particle beam into light. In addition, light emission in the invention includes light emission that uses fluorescence or another light emission phenomenon.

In addition, a thin film or a minute particle coated with a fluorescent agent that emits fluorescence by being irradiated with the charged particle beam may also be used. Examples of the coating material include fluorescent proteins such as a green fluorescent protein (GFP). The color of fluorescence is not limited to green and may be any color such as blue or red. Particularly, GFP that is not instantaneously degraded if being irradiated with the charged particle beam is favorable. For example, an enhanced green fluorescent protein (enhanced GFP; EGFP) is favorable. In the case of the specimen desired to be observed being a biological specimen such as a cell, the effect of good adhesion between GFP, which is a protein, and the cell specimen or the like is achieved. In addition, observation may be performed after increasing the fluorescence intensity of GFP by irradiating, with the charged particle beam after mounting the specimen, a substrate to which GFP is applied, or the specimen may be mounted after increasing the light emission intensity of GFP by irradiating the substrate with the charged particle beam before mounting the specimen. In this case, the coating material is supported by or applied or sprayed to the transparent base 501 not illustrated. In the present embodiment, members, including those above, that generate light by receiving the charged particle on a light receiving surface will be collectively referred to as a light-emitting member. The inelastic mean free path of the charged particle beam is a few tens of nm to a few tens of μm, though depending on an accelerating voltage of the charged particle beam. Thus, a light-emitting region on the upper surface of the detecting element 500 is a region having approximately the same thickness from the surface of the detecting element. Thus, the thickness of the detecting element 500 preferably resides above this thickness. Meanwhile, as described above, in the case of considering optical microscopic observation performed with the same specimen base, the detecting element is required to allow transmission of the optical transmission signal at the time of observation in the optical microscope as far as possible. Thus, the detecting element in the case of having a few mixed colors is preferably as thin as possible.

In the case of the optical microscope 602 being a fluorescence microscope, a fluorescent material is required to be injected into the specimen. In this case, a fluorescence wavelength band of the fluorescent material injected into the specimen is desirably shifted from a light emission wavelength band of the fluorescent material as the light-emitting member in the present embodiment. For example, in the case of coating the detecting element 500 with a green fluorescent protein, the specimen is desirably dyed with a fluorescent protein of red, blue, or the like. In the case of coating the light-emitting member and dying the specimen in the same color, a difference in light emission intensity instead of color is preferably identified under the fluorescence microscope. In addition, in the case of the specimen including the fluorescent material, light from the specimen base 500 and light from the specimen are detected in the optical detector 503 in the charged particle beam device regardless of the color of the fluorescent material. In this case, if a detector having different amplification rates of the light emission wavelength is used in advance as the optical detector 503, transmission information of the charged particle can be acquired as a result. Specifically, if the optical detector 503 that has a higher amplification rate of light from the light-emitting member than an amplification rate of light from the specimen is used, a transmission signal of the charged particle can be selectively amplified.

A transparent specimen base such as a slide glass (or a preparation) or a dish (or a Petri dish) is a specimen base that is generally used in the optical microscope. That is, if the specimen base 500 that includes the detecting element capable of converting the charged particle beam into light in the present embodiment is placed on a shape of a general slide glass (for example, approximately 25 mm×approximately 75 mm×approximately 1.2 mm) for the optical microscope, a user can operate the specimen, mount the specimen, or observe the specimen with previously used experiences or senses. A specimen base that emits light by forming the specimen base such as a slide glass or a Petri dish as the light-emitting member may also be used. Accordingly, the specimen base can be used in such a manner that specimens of observation targets are primarily screened with the optical microscope and that a selected specimen is observed in detail with the charged particle microscope. In addition, since preparation of the specimen in a general high-performance transmission charged particle beam microscope device requires a significant effort, observation with the specimen base in the present embodiment allows screening before observation with the high-performance transmission charged particle beam microscope. In addition, as described later, if positional information or the like is mapped and shared on a computer or on a paper at the time of moving the specimen between microscopes, the same part can be observed with each microscope.

As described above, the inelastic mean free path of the charged particle beam is a few tens of nm to a few tens of μm, though depending on the accelerating voltage of the charged particle beam. Thus, a thin film 502 that is sufficiently thinner than the mean free path may be arranged between the detecting element 500 and the specimen. That is, the specimen is mounted on the thin film 502 that covers the detecting element 500. This specimen base is illustrated in FIG. 3(a). The thickness is described by A in the drawing. The thin film 502 is required to have a thickness and a material that allow transmission of at least a part of the charged particle beam. Since observation is also performed with the optical microscope, the thin film 502 is further required to be transparent with respect to light. If the thin film 502 is arranged, stain, scratch, or the like on the surface of the detecting element 500 can be prevented. As the thin film 502, a substance for increasing adhesion between the specimen and the specimen base in order for the specimen not to be separated from the specimen base may be applied to the specimen base. For example, in the case of the specimen being a biological specimen such as a cell, the surface of the cell is in a negatively charged state due to a lipid bilayer of phospholipid. Thus, applying a molecule (lysine, aminosilane, or the like) in a positively charged state onto the specimen base such as a slide glass can prevent the cell specimen from being peeled from the specimen base. Thus, a molecule in a positively charged state may also be attached to the detecting element 500. A material having hydrophilicity may also be applied in order to facilitate mounting of the specimen in a state including a large amount of liquid. A material having high affinity with a biological specimen such as collagen may also be applied in order to facilitate mounting or culturing of a living cell or germ. The meaning of application widely includes methods for attaching the coating material to the surface of the specimen base, such as spraying, immersion, and coating. The molecule or film may be arranged in only a predetermined position as in FIG. 3(b). The predetermined position means a region of a part of the detecting element 500. For example, in the case of the specimen being a biological specimen such as a cell, arranging a molecule in a positively charged state in only the predetermined position allows arranging the specimen in only the predetermined position. The present technique is useful in the case of, for example, desiring to decrease observation time by narrowing a region desired to be observed. In addition, a conductive member (anti-charging member) may be included on at least a surface on which the specimen is mounted, in order to prevent occurrence of electric charging at the time of irradiation with the charged particle beam. The conductive member is, for example, a carbon material, a metal material, indium tin oxide (ITO), or a conductive organic substance. The above film may have a plurality of layers.

In addition, in the case of the specimen being a hydrated specimen or the like, a thin film 702 may be arranged to surround or cover the observed specimen as in FIG. 4(a). The thin film 702 is, for example, a surface-active material or an organic substance. Arranging the thin film 702 around the specimen can prevent moisture evaporation from the specimen or change of the shape of the specimen. A replacement substance 703 may also be introduced inside or around the specimen as in FIG. 4(b). The replacement substance 703 is, for example, an organic substance such as an ionic liquid. The ionic liquid has a property capable of imparting conductivity to an electron-irradiated surface. Arranging the ionic liquid in or around the observed specimen can prevent electric charging of the specimen at the time of irradiation with the charged particle beam in a vacuum. Furthermore, replacing moisture in the specimen with the ionic liquid can maintain a state of the form of the specimen being maintained. Thus, a transmission image of a wetter specimen can be acquired by detecting light emission with the charged particle beam that is transmitted or scattered by the specimen including the ionic liquid. A method for mounting the ionic liquid in the specimen may be impregnating the specimen in the ionic liquid or may be blowing the ionic liquid to the specimen with a spray or the like.

Hereinafter, an optical detection method that uses the specimen base of the present embodiment and a principle that allows acquisition of a transmitted charged particle beam will be described. FIG. 5 illustrates a state of the specimen 6 being arranged on the detecting element 500. The optical detector 503 is illustrated below the specimen base. The optical detector 503 can convert or amplify an optical signal from the detecting element 500 into an electrical signal. The converted or amplified electrical signal is input into a control unit or a computer through a communication line and is imaged by a control system thereof. The acquired image (transmitted charged particle beam image) may be displayed on a monitor or the like.

The specimen is considered to have a high-density part 508 and a low-density part 509. In the case of irradiating the high-density part 508 in the specimen with a primary charged particle beam 510, most of the charged particle beam is backscattered. Thus, the charged particle beam does not reach the detecting element 500. Meanwhile, in the case of irradiating the low-density part 509 in the specimen with a primary charged particle beam 511, the charged particle beam can be transmitted to the detecting element 500. Consequently, a difference in density inside the specimen can be detected (that is, converted into an optical signal) in the detecting element 500. This manner of transmission changes according to an accelerating energy of the charged particle beam. Thus, changing the accelerating energy of the charged particle beam allows selection of the density of an imaged specimen internal structure. That is, inside information and a region desired to be observed can be changed. In addition, changing the amount of a beam current of the charged particle beam can change a beam diameter. Consequently, the relative size between the size of an observed internal structure and the beam diameter can be changed. That is, changing the beam current can make the inside information desired to be observed seen or not seen.

While a space may exist between the optical detector 503 and the specimen base (a part h in the drawing), the light transmission portion h is preferably as short as possible in order to detect light as efficiently as possible. An optical lens, a mirror, or the like may also be arranged in the light transmission portion h to condense light. The light transmission portion h may be in the air or may be in a vacuum. A solid material that allows passage of the wavelength region of light emission is a material that is transparent or semi-transparent with respect to light, such as quartz, glass, optic fiber, or plastic. With this configuration, the optical detector 503 can be arranged to be separated from a stage. Thus, an interconnect or an electrical circuit connected to the optical detector 503 can be arranged in a position separated from the specimen base or a specimen stage holding the specimen base. In either way, the light transmission portion h is preferably a region that passes the wavelength region of light emission as far as possible. While the optical detector 503 is arranged on the lower side of the specimen base 500 in FIG. 5, the optical detector 503 may be arranged in the horizontal direction with or on the upper side of the specimen base 500 and may be in any position provided that the optical detector 503 can acquire light from the detecting element 500.

A method for mounting the specimen on the specimen base will be described below. The specimen is required to be thin because the charged particle beam (furthermore, light in the case of using optical microscopic observation together) has to be transmitted. For example, the specimen has a thickness of a few nm to a few tens of μm. Examples of the specimen that can be directly mounted on the detecting element 500 include a liquid biological sample such as a liquid including a cell, a mucous membrane, blood, or urine; a sliced cell; a particle in a liquid; a minute particle such as a germ, a fungus, or a virus; and a soft material including a minute particle, an organic substance, or the like. The following methods are considered as mounting methods for the specimen in addition to the above culturing. For example, there is a method of dispersing the specimen in a liquid and attaching the liquid to the detecting element. In addition, the specimen may be sliced to have a thickness allowing transmission of the charged particle beam, and the sliced specimen may be arranged on the detecting element. More specifically, for example, the specimen maybe attached to a tip end of a cotton swab and applied onto a detector, or the specimen maybe dripped with a pipette. In addition, in the case of a minute particle, the minute particle may be sprinkled on the detector. The specimen may also be applied with a spray or the like. A spin coating method of applying a liquid to the specimen base by high-speed rotation may also be used. A dip coating method of performing application by immersing the specimen base in a liquid and pulling up the specimen base may also be used. Any of the methods maybe used provided that the thickness of the specimen can be a thickness of approximately a few nm to a few tens of μm.

<Description of Principle of Three-Dimensional Internal Structure Observation>

Next, a principle for performing three-dimensional internal structure observation of the specimen with use of the charged particle beam will be described by using FIGS. 6-1(a) to 6-3(c). The drawing illustrates a mutual relationship between the specimen 6 and irradiation with a charged particle beam 900. In the specimen 6, a substance 904 that has comparatively low density has an internal substance 901, an internal substance 902, and an internal substance 903 that have comparatively high density. The internal substance 903 has a small size and low density compared with the internal substances 901 and 902. If, for example, a cell specimen is considered as the specimen, the substance 904 is the inside of the cell, and the internal substances 901, 902, and 903 and the like correspond to cell organelles such as a cell nucleus.

An optical axis 905 that is the axis of a charged particle optical column is in the vertical direction in the drawing. Considered is irradiating the specimen 6 with the charged particle beam 900, scanning the charged particle beam 900 in the left-right direction on the page of the drawing, and consequently displaying a signal of an optical signal converted by the detecting element 500 on the monitor as a microscope image. In FIG. 6-1(a), most of the incident charged particle beam 900 is backscattered by the internal substances 901 and 902 having high density, while most of the charged particle beam passes the internal substance 903 having low density. Consequently, an image that is detected on the lower side of the specimen by scanning of the charged particle beam is a projected image (or a detected image or a transmitted charged particle image) 906. For example, the distance between the internal substance 901 and the internal substance 902 in the projected image 906 is not an actual distance and is a distance C projected from above. Since most of the charged particle beam passes the internal substance 903 and cannot be detected, the internal substance 903 does not appear in the projected image 906.

Next, FIG. 6-1(b) is a descriptive diagram in the case of making an incident energy E of the charged particle beam 900 smaller than in the case of FIG. 6-1(a) and is a projected image acquired in that case. The magnitude of the incident energy E is explicitly illustrated by the thickness of an arrow in the drawing. If the incident energy E is low, the intensity of the charged particle beam that cannot pass the internal substance 903 and is backscattered is increased. Thus, an internal structure 903a is detected in addition to the structures of the internal substances 901 and 902 in a projected image (or a detected image) 907. This is based on a phenomenon that a charged particle beam of low energy is more likely to be scattered by a substance.

A three-dimensional positional relationship among the internal substance 901, the internal substance 902, and the internal substance 903 is not apparent from the projected images acquired in FIG. 6-1(a) and FIG. 6-1(b). Therefore, a plurality of projected images is acquired by changing the relative angle between the incident direction of the charged particle beam and the specimen. Specifically, the specimen is inclined, or incidence of the charged particle beam is inclined with respect to the optical axis 905. Three-dimensional positional arrangement of the internal structure can be recognized on the basis of the plurality of projected images. This is exemplified by, for example, a method of inclining an irradiation column, a method of beam tilt of an irradiation beam with an electric field or a magnetic field, or a method of inclining the specimen base, and this can also be realized by a combination of two or more of these methods. FIG. 6-1(c) illustrates a state of irradiating the specimen 6 with the charged particle beam slantwise by inclining the specimen base 500 by θ. If the projected image 907 is compared with a projected image (or a detected image) 908, the distances among the internal substance 901, the internal substance 902, and the internal substance 903 are changed (a part C' and a part D' in the drawing). Furthermore, the size of the substance 904 is changed (a part B' in the drawing). That is, finding the amount of change by observing the projected image 907 and the projected image 908 in comparison allows three-dimensional internal structure observation of the entirety and the inside of the specimen 6.

In addition, a method for realizing three-dimensional internal structure observation inside the specimen by moving the specimen in a rotation direction φ instead of or in addition to the relative irradiation angle θ at the time of irradiation of the specimen with the charged particle beam will be described below. First, the relative angle θ of the specimen with respect to the incident direction of the charged particle beam is made from a state illustrated in FIG. 6-2(a). At this point, the specimen may be inclined by using the specimen stage holding the specimen, the specimen may be inclined in advance and arranged, or the direction of irradiation with the charged particle beam may be inclined. In the example of FIG. 6-2(b), the relative angle θ may be fixed to an angle other than 0°.

At this point, the specimen and the direction of irradiation with the charged particle beam may be changed not by using the specimen stage but by using an inclining mechanism (unit) disposed in the specimen base 500 as in FIG. 20 described later. In this case, the specimen can be inclined on an inclination axis that is different from an inclination axis of the specimen stage. Thus, the specimen can be inclined without restrictions by an inclinable range of the specimen stage. In the case of a device with the specimen stage not having an inclining function, the "different inclination axis" may indicate any position in a specimen chamber.

In a general charged particle beam device, the maximum inclination range of the specimen stage may be approximately 5 degrees to 30 degrees, and only a single side of the specimen stage may be inclined in the case of significantly inclining the specimen stage. While a device used may have a specimen stage capable of significant inclination, inclining the specimen stage with use of another inclining mechanism is effective in the case of the device not having such a specimen stage.

In addition, if the specimen is inclined by using an inclining mechanism that has an inclination axis closer to the optical axis than to the inclination axis of the specimen stage, spatial movement of the specimen required for inclination is reduced, and the effect of being able to ease a spatial restriction on the specimen chamber is also achieved.

Next, the specimen is rotated about an axis R that is perpendicular to the surface of the specimen base 500. While the axis R is perpendicular to the surface of the specimen base 500 for convenience of description, subsequent image processing calculation can be simplified if the axis R is substantially perpendicular thereto.

In addition, as described in FIGS. 7-1 to 7-3(*c*), the axis R is a rotation axis of the specimen stage or a rotating mechanism arranged on the specimen stage. In this case, if the surface of the specimen base 500 is inclined with respect to the ground, the axis R is not perpendicular to the surface of the specimen base 500. However, even in this case, a three-dimensional structure inside the specimen can be built by the same method as the present embodiment. Therefore, hereinafter, the axis R means the rotation axis of the specimen stage or the rotating mechanism that is arranged on the specimen stage and rotates the specimen.

In the case of setting an initial state as FIG. 6-2(*b*) with the horizontal direction in the drawing denoted by an X axis and the vertical direction in the drawing denoted by a Y axis in a projection diagram in a lower part of FIG. 6-2, a plane that includes the X axis and the Y axis is rotated about the axis R. Given that the rotation angle is φ, a plurality of projected images can be acquired by changing the rotation angle φ, and three-dimensional positional arrangement of the internal structure can be recognized on the basis of the result of acquisition. For example, if the specimen base 500 is rotated at the rotation angle φ of 90° from FIG. 6-2(*b*), FIG. 6-2(*b*) becomes FIG. 6-2(*c*). If the specimen base 500 is further rotated at the rotation angle φ of 90° from FIG. 6-2(*c*), FIG. 6-2(*c*) becomes FIG. 6-2(*d*). As is understood from the drawing, if a projected image 916 is compared with a projected image (or a detected image) 918, the distances among the internal substance 901, the internal substance 902, and the internal substance 903 are changed (a part E' and a part F' in the drawing). Furthermore, the size and the shape of the substance 904 in the projected image are changed (a part G' in the drawing). That is, finding each amount of change by comparing and observing the acquired projected images allows three-dimensional internal structure observation of the entirety and the inside of the specimen 6.

In the case of changing the angle θ of the specimen, all of the specimen, the specimen base, and the specimen stage are inclined. Thus, the position of a member including the specimen is required to be significantly moved below the charged particle optical column. That is, according to a device configuration, the inclination angle θ of the specimen may be restricted to a narrow range by a spatial restriction on the specimen chamber or by a movable range or the like of the inclining mechanism such as the stage. Accordingly, in the case of being unable to sufficiently incline the specimen, the amount of information required in the case of performing tomography or the like may not be acquired.

Meanwhile, a configuration that performs rotation at the specimen rotation angle φ just rotates a part of the specimen, the specimen base, and the specimen stage. Thus, the position of the member including the specimen is not required to be significantly moved below the charged particle optical column. That is, since a rotation operation is performed in the plane of the specimen base 500, a space required according to the rotation angle is not significantly increased, and rotation can be easily performed at the angle φ of a large angle (for example, 360 degrees). Thus, in the case of desiring to make the specimen very close to the charged particle optical column, in the case of the specimen chamber having a narrow space, or the like, a configuration that has the irradiation angle θ fixed in advance and then performs rotation at the specimen rotation angle φ is desirable.

In addition, although not illustrated, changing a beam current amount I of the charged particle beam can change the beam diameter. Consequently, the relative size between the size of an observed internal structure and the beam diameter can be changed. That is, changing the beam current can make the inside information desired to be observed seen or not seen. That is, in order to separate information desired to be seen from information not desired to be seen, the beam current amount I of the charged particle beam may be a vector parameter.

To sum up the description heretofore, the relative irradiation angle θ (or the specimen rotation angle φ), the charged particle beam energy E, and the beam current amount I of the charged particle beam at the time of irradiation of the specimen with the charged particle beam are important in order to perform three-dimensional internal structure observation. These are a vector of the charged particle beam. This state will be described by using FIG. 6-3. In the case of considering a specimen internal structure 914 that is configured by linking a plurality of specimen internal structures with lines in FIG. 6-3(*a*), if the irradiation angle θ is changed as in FIG. 6-3(*b*), or if the specimen rotation angle φ is changed in the inclined state of the specimen as in FIG. 6-3(*c*), the orientation of the specimen internal structure 914 with respect to the incident direction 905 of the primary charged particle beam is changed. In addition, if the charged particle beam energy E and the beam current amount I of the charged particle beam are changed, the depth of intrusion of the incident direction 905 of the primary charged particle beam in the depth direction of the specimen internal structure 914 is changed. That is, in the case of the position of the specimen internal structure 914 being considered constant, changing the irradiation angle θ, the specimen rotation angle φ, the charged particle beam energy E, and the beam current amount I of the charged particle beam can change the vector (orientation and intensity) of the charged particle beam as a result. Therefore, in the present specification, with a set of the relative irradiation angle θ or the specimen rotation angle φ between the incident direction of the primary charged particle beam and the specimen, the incident energy E of the primary charged particle beam, and the beam current amount I of the charged particle beam, one or more of any or corresponding elements of the set will be referred to as a vector parameter.

That is, the vector parameter refers to a parameter that determines a mutual relationship between the primary charged particle beam and the specimen. That is, controlling the irradiation angle θ (or the specimen rotation angle φ), the charged particle beam energy E, and the beam current amount I of the charged particle beam as vector parameters determining the vector allows observation of the internal structure of the specimen on the specimen base 500 on the basis of a plurality of images acquired by irradiation with the primary charged particle beam under conditions of different vector parameters. The plurality of images is transmitted charged particle images corresponding to each vector parameter. A three-dimensional internal structure can be identified by acquiring the plurality of images with change of the vector parameters of the irradiation angle θ (or the specimen rotation angle φ), the charged particle beam energy E, and the beam current amount I of the charged particle beam and by lining up and observing or successively displaying these images. In addition, the three-dimensional internal structure can be quantified by measuring the size of the internal structure such as a distance or an area and comparing several images. While only a measurement result may be displayed with this calculation performed in a computer, displaying an intermediate image to an operator has an advantage of allowing confirmation of the validity of the result. Hereinafter, "change of the vector parameter" means changing or controlling at least one of the relative irradiation angle θ (or the specimen rotation angle φ) between the incident direction of the primary charged particle beam and the specimen, the incident energy E of the primary charged particle beam, and the beam current amount I of the charged particle beam.

In addition, the inside information may be desired to be promptly acquired in real time. For example, as described later, the specimen may be automatically moved and subjected to tomography by a computed tomography (CT). In this case, the time of the specimen being arranged in the charged particle beam device is limited. Thus, in such a case, the irradiation angle θ (or the specimen rotation angle φ), the charged particle beam energy E, and the beam current amount I of the charged particle beam may be changed as a set in real time. Consequently, the inside information desired to be seen can be promptly observed.

<Description of Device>

FIG. 7-1 describes a device that can perform three-dimensional internal structure observation with the specimen base of the present embodiment mounted therein. The charged particle microscope is mainly configured of a charged particle optical column 2, a casing 7 (hereinafter, may be referred to as a vacuum chamber) that supports the charged particle optical column with respect to a device installation surface, and a control system that controls the charged particle optical column 2 and the casing 7. When the charged particle microscope is used, the insides of the charged particle optical column 2 and the casing 7 are evacuated to be a vacuum by a vacuum pump 4. Start and stop operations of the vacuum pump 4 are also controlled by the control system. While only one vacuum pump 4 is illustrated in the drawing, the vacuum pump 4 maybe greater than or equal to two in number.

The charged particle optical column 2 is configured of elements of a charged particle source 8 that generates the primary charged particle beam, an optical lens 1 that concentrates and guides the generated charged particle beam to a lower portion of the column to scan the primary charged particle beam on the specimen 6, and the like. The charged particle optical column 2 is installed to protrude into the casing 7 and is fixed to the casing 7 through a vacuum seal member 123. A detector 3 that detects a secondary charged particle (a secondary electron, a reflective electron, and the like) acquired by irradiation with the primary charged particle beam is arranged in an end portion of the charged particle optical column 2. The detector 3 may not be in the position illustrated and may be in any position inside the casing 7.

The secondary charged particle such as a reflective charged particle or a transmitted charged particle is emitted from the inside or the surface of the specimen by the charged particle beam arriving at the specimen 6. The secondary charged particle is detected in the detector 3. The detector 3 is a detecting element that can detect and amplify the charged particle beam arriving at an energy of a few keV to a few tens of keV. The detector 3 is, for example, a semiconductor detector made of a semiconductor material such as silicon or a scintillator capable of converting a charged particle signal into light on a glass surface or in the inside thereof.

A vacuum pipe 16 that has one end thereof connected to the vacuum pump 4 is connected to the casing 7, and the inside of the casing 7 can be maintained in a vacuum state. In addition, a leak valve 14 for opening the inside of the casing to the atmosphere is included, and the inside of the casing 7 can be opened to the atmosphere at the time of introducing the specimen base in the device. The leak valve 14 may not be included or may be greater than or equal to two in number. In addition, the arrangement location of the leak valve 14 in the casing 7 is not limited to a location illustrated in FIG. 7-1, and the leak valve 14 may be arranged in another position on the casing 7.

The casing 7 includes an opening portion in a side surface thereof. A lid member 122 and a vacuum seal member 124 in the opening portion maintain the inside of the device to be an airtight vacuum. The charged particle microscope of the present embodiment includes a specimen stage 5 for changing a positional relationship between the specimen and the charged particle optical column after putting the specimen mounted on the specimen base into the casing 7 as described above. The above light-emitting member or the specimen base having the light-emitting member is attachably and detachably arranged in the specimen stage 5. A supporting plate 107 that is a bottom plate supported by the lid member 122 is attached to the specimen stage 5, and the stage 5 is fixed to the supporting plate 107. The stage 5 includes an XYZ driving mechanism in an in-plane direction or in the height direction and an inclination driving mechanism that can incline the specimen with respect to an optical axis 200 of the charged particle optical column. If the stage 5 is changed, the specimen angle θ can be changed. In addition, the specimen stage 5 including a rotation driving mechanism capable of rotation with the optical axis direction as an axis can change the specimen rotation angle φ. In addition, a driving mechanism that can perform rotation or inclination and is configured as a separate body from the specimen stage 5 may be arranged on the specimen stage 5. The supporting plate 107 is attached to extend toward a facing surface of the lid member 122 and into the casing 7. Spindles extend from each of several driving mechanisms of the stage 5 and are respectively connected to a driving unit 51 and a driving unit 52 of the lid member 122. While only two driving units are illustrated in the drawing, driving units are arranged in the same number as the driving mechanisms. The driving unit 51 and the driving unit 52 are electric motors or the like. The driving unit 51 and the driving unit 52 may be rotated manually by the user. The device user can adjust the position of the specimen by manually operating the driving units 51 and 52 or inputting an instruction into a higher control unit with a user interface 34. In addition, although not illustrated, if the optical microscope is included in the casing 7, simultaneous observation can be performed with two or more microscopes, or an effort of movement or positioning between specimen chambers can be reduced.

The detecting element 500 on which the specimen is mounted can be mounted on the specimen stage 5. As described above, the charged particle beam is converted into light in the detecting element 500. The optical detector 503 for detecting and converting the light into an electrical signal and amplifying the signal is included on the specimen stage 5 or near the stage. As described above, the optical detector 503 is desirably arranged to be capable of efficiently detecting the optical signal. For example, the specimen base including the detecting element 500 and the optical detector may be close to each other or may be in contact or not. The light transmission portion h may also be arranged between the specimen base and the optical detector 503. While the optical detector is included in the specimen stage in FIG. 7-1, the optical detector 503 may be fixed to some place in the casing 7 to detect light emission from the specimen base 500. In addition, the optical detector 503 may be installed outside the casing 7, and light may be guided and detected outside the casing 7. In the case of the optical detector 503 being outside the casing 7, a signal can be detected in the optical detector by including a light transmission path, such as glass or optical fiber, for transmission of light near the specimen base 500 and transmitting the optical signal converted in the detecting element 500 through the light transmission path. The optical detector 503 is, for example, a semiconductor detecting element or a photomultiplier. In either way, the optical detector of the present embodiment detects light emitted in the above detecting element of the specimen base.

FIG. 7-1 illustrates a state of the optical detector 503 being included in an upper portion of the stage 5. A preamplifier substrate 505 is connected to the optical detector 503 included in the stage 5 via an interconnect 509. The preamplifier substrate 505 is connected to a lower control unit 37 via an interconnect 507 and the like. While the preamplifier substrate 505 is inside the casing 7 in the drawing, the preamplifier substrate 505 may be outside the casing 7 (for example, a preamplifier 54 in the drawing). As described later, the specimen base 500 is required not to fall from the specimen stage 5 at the time of inclining the specimen base 500. Thus, a fixing member 506 that can determine a position to arrange the specimen base 500 on the specimen stage 5 is included. In addition, a fixing member not illustrated may be between the specimen base 500 and the optical detecting element 503. Accordingly, the specimen base 500 can be fixed, and positional shift thereof can be prevented.

Both the detector 3 and the detecting element 500 are in the charged particle beam device of the present embodiment. Thus, the secondary charged particle generated or reflected from the specimen can be acquired in the detector 3, and at the same time, the transmitted charged particle transmitted or scattered by the specimen can be acquired in the detecting element 500. Therefore, display of a secondary charged particle beam image and a transmitted charged particle image on a monitor 35 can be switched by using the lower control unit 37 or the like. In addition, the two types of images can be displayed at the same time.

The control system of the charged particle microscope of the present embodiment includes a higher control unit 36 to which the user interface 34 such as a keyboard or a mouse used by the device user or the monitor 35 displaying a microscope image is connected and communicates, the lower control unit 37 that controls an evacuation system, a charged particle optical system, and the like in accordance with an instruction sent from the higher control unit 36, and a stage control unit 38 that sends and receives signals with the driving unit 51 and the driving unit 52. Each unit is connected by communication lines. The stage control unit 38 and the lower control unit 37 may be arranged in one unit or may be arranged inside the higher control unit 36.

The lower control unit 37 has means for sending and receiving control signals for controlling the vacuum pump 4, the charged particle source 8, the optical lens 1, and the like. More specifically, the lower control unit 37 has means for controlling the vector parameter in order to perform the above three-dimensional internal structure observation. That is, the lower control unit 37 can change and control the energy E of the charged particle beam from the charged particle beam source 8 until reaching the specimen and the irradiation angle θ (or the specimen rotation angle φ). In the drawing, an irradiation energy control unit 59 is illustrated between the lower control unit 37 and the charged particle optical column 2. The irradiation energy control unit 59 includes a high-voltage power supply or the like that can determine the energy E of irradiation of the specimen with the charged particle beam. The high-voltage power supply or the like having the function of the irradiation energy control unit 59 may be inside the lower control unit 37.

Change of the energy E of irradiation of the specimen with the charged particle beam can be achieved by changing an accelerating voltage from the charged particle beam source or by changing a voltage to the optical lens that can accelerate or decelerate the charged particle beam before irradiation of the specimen with the charged particle beam. A power supply that can apply a voltage to the specimen stage may also be included.

Change of the irradiation angle θ can be performed by controlling the optical lens that can incline the charged particle beam with respect to the optical axis 200 to perform irradiation. A mechanism that inclines the charged particle optical column 2 may also be included. In addition, the lower control unit 37 includes an A/D converter that converts an analog signal from the detector 3 or the optical detector 503 into a digital image signal and sends the digital image signal to the higher control unit 36. Digital image signal data is sent to the higher control unit 36. An analog circuit, a digital circuit, and the like maybe mixed in the lower control unit 37, and the higher control unit 36 and the lower control unit 37 may be integrated.

Information of stage position adjustment is transmitted from the higher control unit 36 to the stage control unit 38. The stage control unit 38 sends, to the driving mechanisms 51 and 52, driving information that is determined in accordance with the information. In addition, the above specimen angle θ and the specimen rotation angle φ which are the vector parameters are controlled in this manner.

In addition, a current control unit for controlling the optical lens that can change the beam current amount I of the charged particle beam is included in the lower control unit 37. Alternatively, the beam current amount I emitted from the electron source 8 may be controlled by the high-voltage power supply as the irradiation energy control unit 59.

Next, the inside of the higher control unit 36 will be described. A data sending and receiving unit 40, a data memory unit 41, an external interface 42, and a calculating unit 43 are included in the higher control unit. The data sending and receiving unit 40 receives data such as a detected image and sends, to the lower control unit 37 or the stage control 38, data for changing the irradiation energy E, the irradiation angle θ, and the specimen rotation angle φ. The data memory unit 41 stores a digital detected signal sent from the lower control unit 37 as data. The external interface 42 sends and receives signals with the user interface 34 such as a keyboard or a mouse used by the device user and the monitor 35 displaying a microscope image. The calculating unit 43 processes calculation of acquired data or operating information from the user. Detected image information may be read from the memory unit 41 and displayed on the monitor 35 or may be stored by storing data in a memory. In addition, the detected image information may be displayed on the monitor 35 in real time. The higher control unit may be a computer such as a personal computer or a workstation or may be a control substrate on which a CPU, a memory, and the like are mounted. The higher control unit 36 can perform calculation process of image data in the calculating unit 43 after storing the image data in the memory unit 41 via the data sending and receiving unit 40, controlling the irradiation energy E, the irradiation angle θ, and the specimen rotation angle φ, which are the vector parameters, via the data sending and receiving unit 40 from the calculation result, and the like.

The configuration of the control system illustrated in FIG. 7-1 is merely one example. Modification examples of a control unit, a valve, a vacuum pump, a communication interconnect, or the like fall within the scope of the charged particle beam microscope of the present embodiment as long as satisfying the function intended in the present embodiment. That is, each control block may be incorporated into one device or may be separately arranged in other devices. In addition, information may be input into another computer by using the measurement result (image information) acquired by this method, and the measurement result may be analyzed or displayed.

In addition, the charged particle beam microscope includes a control unit controlling operation of each part and an image generating unit generating an image on the basis of a signal output from the detector (not illustrated). The control unit and the image generating unit may be configured of dedicated circuit substrates as hardware or may be configured of software executed by a computer connected to the charged particle beam microscope. In the case of a hardware configuration, the hardware configuration can be realized by integrating a plurality of calculators executing processes on an interconnect substrate or a semiconductor chip or in a package. In the case of a software configuration, the software configuration can be realized by mounting a high-speed general-purpose CPU in a computer and executing a program executing a desired calculation process. The existing device can also be updated with a recording medium in which the program is recorded. In addition, the device, the circuit, and the computer are connected by a wired or wireless network in addition to the illustrated communication line to appropriately send and receive data.

FIGS. 7-2(a) and 7-2(b) are diagrams illustrating an arrangement relationship among members near the specimen 6, the detecting element 500, and the optical detector 503. While FIG. 7-2(a) is a top view of these members, the specimen stage 5 is not illustrated for easy understanding. FIG. 7-2(b) is a side view of FIG. 7-2(a). Details of arrangement of the charged particle optical column 1, the driving mechanisms of the specimen stage 5, the optical detector 503, the specimen 6, and the like in the case of the vector parameter of the specimen rotation angle φ will be described by using FIGS. 7-2(a) to 7-2(b).

In FIGS. 7-2(a) to 7-2(b), the optical detector 503 is arranged in some place on the charged particle optical column 1 side from the surface of the specimen 6. In the present embodiment, in the case of using the rotating mechanism in combination as described in FIGS. 6-2(a) to 6-2(d), the specimen stage 5 desirably has a mechanism for inclining the specimen (a part T in the drawing: inclining stage), and a mechanism rotating the specimen (a part R in the drawing: rotating stage). The inclining mechanism or the rotating mechanism that can move independently of the stage 5 may also be included on the stage 5 as described later. The specimen stage 5 may have a mechanism moving the specimen in the vertical or horizontal direction (a part XY in the drawing: XY stage) and a height adjusting mechanism capable of changing the distance between the specimen and the charged particle optical column 1.

A direction in which the angle θ is driven by the mechanism of the specimen stage 5 for inclining the specimen 6 (the part T in the drawing) is required to be in the direction of the optical detector 503. For example, in the case of the optical detector 503 being arranged on the left side of the drawing of the charged particle optical column 1 with the inclination axis thereof in the perpendicular direction of the page of the drawing as illustrated in FIG. 7-2(b), the angle θ is required to be adjusted to direct the specimen 6 to the left side of the drawing. Given that an axis perpendicular to a detecting surface of the optical detector 503 is an axis a and that the rotation axis of the rotating mechanism rotating the specimen is an axis b, ideally, the axis a and the axis b are desirably equal to each other (as illustrated in FIG. 7-2(a), the axis a and the axis b match in the case of a view from the top). In the case of being unable to perform inclination to the direction of the detector, the axis a and the axis b may be in the range of an angle η as an optical detector 503' or an optical detector 503". The range of the angle η is maximum 180 degrees. In addition, in order to observe a three-dimensional internal structure in the present embodiment, the mechanism rotating the specimen (the part R in the drawing) is desirably on the mechanism for inclining the specimen (the part T in the drawing) as illustrated in the drawing. In this case, a positional relationship between the optical axis 200 and the specimen base 500 becomes constant at all times in the case of rotating the specimen 6 about the rotation axis b. In the case of the mechanism for inclining the specimen (the part T in the drawing) being on the mechanism rotating the specimen (the part R in the drawing), if the specimen is rotated about the rotation axis b, a problem arises in that the mechanism for inclining the specimen (the part T in the drawing) is also rotated. Thus, in the case of acquiring an image with change of the specimen rotation angle φ of the vector parameters, the specimen stage 5 is desirably configured by arranging the mechanism rotating the specimen (the part R in the drawing) on the mechanism for inclining the specimen (the part T in the drawing).

Next, details of the charged particle optical column 1, the driving mechanisms of the specimen stage 5, the optical detector 503, the specimen 6, and the like in the case of acquiring an image with change of the irradiation angle θ of the vector parameters will be described by using FIGS. 7-3(a) to 7-3(c). FIGS. 7-3(a) to 7-3(c) are diagrams illustrating an arrangement relationship among members near the specimen 6, the detecting element 500, and the optical detector 503. While FIG. 7-3(a) is a top view of these members, the specimen stage 5 is not illustrated for easy understanding. FIGS. 7-3(b) and 7-3(c) are side views of FIG. 7-3(a) and illustrate the arrangement seen from the lower side in FIG. 7-3(a). FIG. 7-3(b) is an example of inclining an inclination axis c to direct the specimen 6 to the left side of the drawing in FIG. 7-3(a), and FIG. 7-3(c) is an example of inclining the inclination axis c to direct the specimen 6 to the right side of the drawing in FIG. 7-3(a).

In FIGS. 7-3(a) to 7-3(c), the optical detector 503 is arranged in some place on the charged particle optical column 1 side from the surface of the specimen 6. In this example, the specimen stage 5 has the mechanism for inclining the specimen (the part T in the drawing) and is required to have a structure capable of changing the inclination angle θ. The specimen stage 5 may have the mechanism moving the specimen in the vertical or horizontal direction (the part XY in the drawing) and the height adjusting mechanism capable of changing the distance between the specimen and the charged particle optical column 1. Even if the angle θ is changed by driving the mechanism of the specimen stage for inclining the specimen (the part T in the drawing), the area at the time of projecting a light-emitting region of the surface of the specimen base in the direction of the optical detector 503 is desirably not significantly changed with respect to the change of the angle θ in order to stably acquire light emitted from the specimen base 500. Ideally, given that the axis perpendicular to the detecting surface of the optical detector 503 is the axis a and that the inclination axis of the inclining mechanism inclining the specimen at the angle θ is the axis c, the axis a and the axis c are desirably equal to each other (as illustrated in FIG. 7-3(a), the axis a and the axis c match in the case of a view from the top). In the case of the axis a and the axis c being equal to each other, only a side surface of the specimen base 500 is seen at all times from the optical detector 503 independently of the angle θ. Thus, the proportion of detectable light intensity in the entire light emission does not depend on the angle θ.

Meanwhile, if the detector is in the position of an optical detector 503''', a problem of light not being detected arises in the case of inclining the specimen to a position in FIG. 7-3(c). That is, if the size of the angle formed by the specimen inclination axis c and the axis a of the optical detector 503 is not within a predetermined range, detectable light intensity in the light emission from the specimen base 500 differs according to the size of the inclination angle θ. Thus, an image acquired has brightness depending on the size of the inclination angle θ, and accurate three-dimensional information may not be acquired.

Thus, in the case of a view from the top as illustrated in FIG. 7-3(a), the optical detector 503 is desirably arranged to fall the angle formed by the specimen inclination axis c and the axis a of the optical detector 503 within ±30°. That is, as illustrated in FIG. 7-3(a), the angle η formed by an axis a' and an axis a'' of the optical detector in arrangeable limit positions of the optical detector 503 is desirably equal to maximum 60° with the specimen inclination axis c at the center of the angle η. Arranging the optical detector to fall the angle formed by the axis c and the axis a within this range allows acquisition of an image having stable brightness independently of the inclination angle and allows acquisition of accurate three-dimensional information from the image. Although not illustrated, a method for acquiring an image having stable brightness independently of the inclination angle may also be a configuration in which members (optical fiber and the like) described in the description of the light transmission portion h are arranged near the specimen to guide light emission from the specimen base 500 to the detector. In this case, while the device configuration is increased to change required detection intensity (light intensity), an image having stable brightness independently of the inclination angle can be acquired.

<Operating Screen>

FIG. 8 illustrates one example of an operating screen. As vector parameter setting units for observing a three-dimensional internal structure, an irradiation energy E changing unit 45, an irradiation angle changing unit 46, a specimen angle changing unit 47, a specimen rotation angle changing unit 60, and the like are displayed on the monitor. The irradiation energy of the charged particle beam is set in accordance with a numerical value that is input into the irradiation energy E changing unit 45. The irradiation angle changing unit 46 is an input window for changing the angle between the charged particle beam and the optical axis, and the irradiation angle with respect to the optical axis of the charged particle beam is set in accordance with an input numerical value. The specimen angle changing unit 47 is an input window where an angle at which the specimen 6 is inclined is input, and the specimen is inclined by inclining the specimen stage in accordance with an input numerical value. The specimen rotation angle changing unit 60 is an input window for changing the rotation angle θ of the specimen, and the specimen is rotated in accordance with an input numerical value.

As described above, the irradiation energy E of the vector parameters corresponds to the density of an observable structure, and the irradiation angle, the specimen angle, or the specimen rotation angle corresponds to the direction of observation. Thus, the input windows on the operating screen may be display items such as "density" and "observation direction". Any of the irradiation angle changing unit 46 and the specimen angle changing unit 47 may not be included. If only the irradiation angle θ is changed, the specimen rotation angle changing unit 60 may not be included. Furthermore, the operating screen is configured of a focal point adjusting unit 48 that changes the focal point of the charged particle beam, an image brightness adjusting unit 49, an image contrast adjusting unit 50, an irradiation start button 51, an irradiation stop button 52, and the like.

Furthermore, the operating screen includes a screen 55 that can display a microscope image in real time, a screen 56 that can display an image stored in the memory unit 41, and the like. The screen 56 that can display an image stored in the memory unit 41 may be displayed in a separate window, and the screen 56 may be greater than or equal to two in number and may display images acquired with different vector parameters on each screen. In addition, an image store button 57 for storing an image and an image read button 58 capable of reading an image are also displayed.

The device user can identify the three-dimensional internal structure of the specimen by acquiring a plurality of images displayed in different states of settings of the irradiation energy E, the irradiation angle θ, and the specimen rotation angle ϕ, which are the vector parameters, and by displaying transmitted charged particle images corresponding to the plurality of vector parameters in parallel. In addition, instead of parallel display or in addition to parallel display, display of these images may be switched in each any amount of time. At this point, displaying the images in order of magnitude of the vector parameters allows the user to more easily recognize the three-dimensional structure. The display configuration illustrated in FIG. 8 is merely one example. Modification examples of a display position, a display form, and the like fall within the scope of the charged particle beam microscope of the present embodiment as long as satisfying the function intended in the present embodiment.

In addition, storing values used in a series of measurement steps as table data in a storage unit (not illustrated) can save an effort of the operator inputting a part of all vector parameters used in the series of measurement steps. In addition, the table data may be stored as data that is associated with the property of the specimen (the type or the film thickness of the specimen), a depth desired to be measured, accuracy, and the like. In this case, the operator inputting the above property of the specimen or the device measuring and automatically determining the specimen has an advantage of saving an effort of inputting each parameter.

<Manual Observation Procedure>

Next, a procedure in which the user observes a three-dimensional internal structure will be described by using FIG. 9.

First, the user prepares the detecting element 500 (light-emitting specimen base) for mounting the specimen. Next, a predetermined member is arranged in the detecting element 500 if necessary. The predetermined member is, as described above, a substance for increasing adhesion between the specimen and the specimen base, a conductive substance, a substance for reflecting light, any predetermined gas material, or the like. If the predetermined member is not required to be arranged, the present step is not required. Next, the user mounts the specimen on the detecting element 500. Next, a transition is made to a step of mounting and observation in the charged particle microscope or in the optical microscope. Step A is a step of observation with the optical microscope, and Step B is a step of observation with the charged particle microscope.

In Step A of observation with the optical microscope, the user first arranges the detecting element 500 on which the specimen is mounted in the optical microscope device. As described above, if the shape of a slide glass is required at the time of arrangement in the optical microscope device, the detecting element 500 can be mounted on a slide glass. Next, the user performs observation with the optical microscope. If the observation is ended, a transition is made to Step B of observation with the charged particle microscope device. As described later, if the optical microscope can acquire digital data, the data may be moved to the higher control unit 36 to display the optical microscope image on the monitor 35.

In Step B of observation with the charged particle microscope, the user first arranges the detecting element 500 on which the specimen is mounted in the charged particle microscope device as described above. Next, in Step 61, the irradiation energy E, the irradiation angle θ (specimen rotation angle φ), or the beam current amount I which is a desired vector parameter is set in an operating screen 44 on the monitor 35. In next Step 62, the specimen is irradiated with the charged particle beam by the charged particle microscope, and light emission from the specimen base 500 is detected. In next Step 63, an image acquired in Step 62 is displayed in the screen 55 on the monitor 35. In next Step 64, a focal point is set in a desired position by adjusting the excitation intensity of the optical lens on the basis of inputs of the user in the above operating screen. In next Step 65, the brightness or the contrast of the image is adjusted in the desired position by changing the amplification rate of a detected signal in the preamplifier substrate 505 on the basis of inputs of the user in the above operating screen. After a desired image is acquired, in next Step 66, image data is stored in the memory unit 41 by storing the image. In next Step 67, the user determines whether or not to change the vector parameter. If the vector parameter is required to be changed, a return is made to Step 61. If the vector parameter is not required to be changed, observation with the charged particle microscope device is ended, and the specimen is taken out of the charged particle microscope device. If necessary, a return is made to Step A of observation with the optical microscope. Step A and Step B may also be switched. In addition, if the charged particle microscope device and the optical microscope device are integrated into a device, Process A and Process B may be alternately repeated, or observation may be performed at the same time. Performing this step allows a three-dimensional internal structure in the specimen observed with the optical microscope to be observed with the charged particle beam microscope.

<Automatic Observation Procedure>

Next, a configuration for automatically performing a series of operations for three-dimensional internal structure observation and a procedure for storing the image in Step B of FIG. 9 will be described. Specifically, this can be performed if Step 61 to Step 67 are automated.

For example, a method for performing three-dimensional internal structure observation with change of the specimen angle θ will be described below by using an operating screen 70 illustrated in FIG. 10. The operating screen 70 includes an initial specimen angle θ setting unit 71, a final specimen angle θ setting unit 72, and a changed angle Δθ setting unit 73 that determines a pitch width between the initial specimen angle θ and the final specimen angle θ. Angle is changed by an angle Δθ set in the changed angle Δθ setting unit 73 at a time from an angle set in the initial specimen angle θ setting unit 71 to an angle set in the final specimen angle θ setting unit 72. The operating screen 70 includes a vertical setting bar 74, a horizontal setting bar 75, and a screen 76 in which a microscope image is displayed. The vertical setting bar 74 and the horizontal setting bar 75 are for specifying an object that determines a position observed at all times at the center of the image at the time of changing the angle θ. A point of intersection of the vertical setting bar 74 and the horizontal setting bar 75 is an automatic image acquisition reference point 77. The user adjusts the positions of the vertical setting bar 74 and the horizontal setting bar 75 in such a manner that the automatic image acquisition reference point 77, which is the point of intersection of the vertical setting bar 74 and the horizontal setting bar 75, matches a position desired to be observed.

A setting method for the automatic image acquisition reference point 77 is not limited to the above method and is preferably means allowing the user to select a specific position in the specimen. In addition, the automatic image acquisition reference point 77 may not be at the center of the screen. In the drawing, a state of the automatic image acquisition reference point 77 being set to match the internal substance 901 is illustrated. If settings are made to the state in the drawing, the internal substance 901 can be at the center of the image at all times even if the inclination θ of the specimen is changed. Furthermore, while the focal point and the brightness of the image are changed if the inclination angle θ is changed, the position, the focal point, and the brightness are automatically adjusted with a part determined by the automatic image acquisition reference point 77 as a reference. The above processes and the control units changing the irradiation angle θ may also change the specimen rotation angle φ.

For example, the position of the internal substance 901 at the center of the screen is moved to a position shifted from the left-right direction in the drawing if the specimen 6 is inclined. Thus, a signal may be transmitted to the driving mechanism 51 via the stage control unit 38 to automatically correct the position in such a manner that the part set as a reference point is not shifted from the center of the screen before and after change of the inclination angle θ or the specimen rotation angle φ which is the vector parameter. The automatic image acquisition reference point may not be fixed to the center of the image. The important point is correcting the position of the stage in such a manner that a specimen position set as the automatic image acquisition reference point in the transmitted charged particle image is not changed. The automatic adjustment is performed with the data sending and receiving unit 40, the data memory unit 41, and the calculating unit 43 in the higher control unit 36 illustrated in FIG. 7-1. Particularly, automatic position recognition is performed by the calculating unit 43 performing image calculation that specifies where a structure at the automatic image acquisition reference point 77 is moved by change of the inclination angle θ or the specimen rotation angle φ. Then, the calculating unit 43 automatically adjusts the focal point to set the focal point in the position of the automatic image acquisition reference point 77 and adjusts brightness to make the brightness in the position of the automatic image acquisition reference point 77 match the brightness before inclination of the specimen. Accordingly, the focal point is set at all times with constant brightness in the specimen position set as the automatic image acquisition reference point before and after change of the inclination angle.

While the automatic image acquisition reference point 77 is illustrated as only one point, the automatic image acquisition reference point 77 may be in plural numbers, and the accuracy of automatic adjustment may be increased by specification on the surface. After these settings are finished, Step 61 to Step 67 illustrated in FIG. 9 can be automatically performed by pushing the automatic acquisition start button 78.

An image acquired between Step 61 to Step 67 is stored in the data memory unit 41. Reading or lining up successive inclination images stored in the data memory unit 41 in order on the monitor allows the device user to identify a three-dimensional internal structure inside the specimen. While only inclination of the specimen is described heretofore, the same applies to the case of changing the irradiation energy E or the irradiation angle θ with respect to the optical axis of the charged particle beam. In that case, the "specimen angle θ" in the above description may be replaced with the "irradiation energy E", "the irradiation angle θ with respect to the optical axis of the charged particle beam", or the "beam current amount I". Images may also be automatically acquired not by changing the specimen inclination angle θ but by changing the specimen rotation angle φ. Furthermore, images may be automatically acquired by changing the vector parameters of the irradiation energy E and the specimen inclination θ at the same time.

Images manually or automatically acquired as described above may be subjected to tomography by computed tomography (CT). In the case of a CT image, a three-dimensional internal structure can be displayed by freely rotating the image on the monitor. Thus, the operator can better observe the internal state of the specimen. Furthermore, only a cross section desired by the operator can be taken and displayed. Configuring a CT image allows acquisition of a cross-sectional image or a slice image without creating a slide or the like of the specimen. In addition, in the case of desiring to promptly subject a specimen such as a cell to CT, the specimen may be automatically moved. In this case, if the irradiation angle θ or the specimen rotation angle φ, the charged particle beam energy E, and the beam current amount I of the charged particle beam can be changed as a set in real time, a large amount of information can be acquired in a short amount of time.

In addition, although not illustrated, stereoscopic observation of stereoscopically observing the two stored or displayed images by inclining the images at a few degrees may be used. At the time of stereoscopic observation, two images captured by changing the angle may be lined up and stereoscopically viewed, an image in which images having two types of colors such as blue and red changed are superimposed may be used, or three-dimensional display may be made on a display unit such as a monitor capable of three-dimensional observation. In addition, while an example subjected to tomography by computed tomography (CT) is considered to provide high convenience of use for the user above, another method may also be used as a formation method for a three-dimensionally built image.

<Immunostaining>

In addition, immunostaining that attaches a label such as colloidal gold may be performed for the specimen. Attaching a label allows observation of not only a morphological structure inside the specimen but also a location of a local existence of a protein or the like to be detected inside the specimen. FIGS. 11(*a*) and 11(*b*) consider the case of observing the specimen by attaching a label. The specimen in this case is, for example, a cultured cell or a cell extracted from a living body. If a material to which an antibody bonded with a gold label 909 is attached is injected into the cell, the material reacts and is coupled specifically with a protein or the like inside the cell (antigen-antibody reaction). The charged particle beam 900 is significantly scattered by the gold label 909. Thus, a projected image (or a detected image) 910 is as in the drawing, and a location where the gold label 909 gathers and locally exists is understood. Consequently, a location of a protein or the like desired to be detected can be recognized.

In addition, performing three-dimensional internal structure observation, CT observation, or the like with change of the vector parameter (change of the specimen angle θ in the drawing) as in FIG. 11(*a*) and FIG. 11(*b*) allows recognition of a location where a protein or the like desired to be detected gathers inside the cell. Furthermore, while the gold label 909 has various sizes of a few nm to a few μm, the amount of the scattered charged particle beam 900 differs according to the gathered amount or the density of the gold label 909. That is, for example, adjusting the irradiation energy E allows detection of a gold label portion 911 having light color (or a gold label portion, not illustrated, having dark color) or the like in the projected image 910. The projected image 910 represents the position, the density, or the like of a specifically gathered protein. Thus, the user can recognize the position or the density of a protein inside the cell by looking at the image. The size, the depth of color, and the like of the above gold label portion may be only enough for observation by the device user, or measurement of the size or determination of the depth of color may be performed in the higher control unit 36.

In addition, although not illustrated, a radial ray such as an X-ray generated by irradiation with the charged particle beam may be acquired. Accordingly, elements or a chemical state inside the specimen can be analyzed.

<Description of Microscope Information Exchange>

As described above, optical microscopic observation and charged particle microscopic observation of the specimen on the same specimen base can be performed by mounting the specimen desired to be observed on the specimen base. At this point, it is desirable to be capable of accurately observing the same part with the optical microscope and the charged particle microscope. Therefore, a device system that can observe the same part with the optical microscope and the charged particle microscope will be described by using FIG. 12. The optical microscope 602 includes a CCD camera 603. The user first acquires an image of the specimen with the optical microscope. The CCD camera 603 and the higher control unit 36 are connected by an interconnect 604. Accordingly, digital image information of the optical microscope can be sent to the higher control unit 36 as illustrated by a dotted arrow in the drawing. In addition, image information acquired with the charged particle microscope is also sent to the higher control unit 36. Thus, the microscope images of the same part can be compared on the same monitor 35. The user can arrange a desired specimen position in an irradiation position of the primary charged particle beam on the basis of an observation result with the optical microscope by finding the specimen position to acquire an image with the charged particle microscope while seeing the image acquired with the optical microscope on the monitor. In addition, a specimen position of a shape similar to the optical microscope image may be found by a calculation process such as image matching or similarity calculation and may be automatically set as the irradiation position of the charged particle beam. Although not illustrated, another computer may be interposed between the optical microscope and the higher control unit, or image information may be sent via a communication line such as the Internet.

In addition, a simple optical microscope 202 may be arranged in the charged particle microscope device 601 as in FIG. 13. "Simple" means, for example, having an advantage of a small size, an inexpensive price, or the like and being able to perform required optical microscopic observation. The optical microscope 202 has a simple imaging system such as an optical lens and a capturing element such as a CCD camera. Image information from the optical microscope 202 is also connected to the higher control unit 36 via an interconnect. In addition, the distance between the optical axis 200 of the charged particle microscope and an optical axis 201 of the optical microscope 202 is constant at all times. Thus, the distance of moving a location is constant at all times after observation with the optical microscope. Thus, if a configuration of storing the distance in advance in a memory or the like and controlling the driving units 51 and 52 with the distance value as the amount of stage movement at the time of an input of a stage movement instruction is used, the user can provide an instruction for movement between the optical axis 200 of the charged particle microscope and the optical axis 201 of the optical microscope 202 with a very simple operation. Therefore, observing the same specimen part with the simple optical microscope 202 and the charged particle microscope 601 makes the user perform an operation very easily and can reduce the size or the cost of the device and thus is efficient.

In addition, as another effect, since any of the optical microscope 602 and the optical microscope 202 is a microscope that uses light, images that look almost the same are acquired. Thus, the same part of the specimen observed with the optical microscope 602 is very easily observed with the charged particle microscope 601. Specifically, observation is performed in the following procedure. The user first observes a desired position in the specimen with the optical microscope 602 installed outside the charged particle microscope device and then introduces the specimen base on which the specimen is mounted into the charged particle microscope device. Next, the position observed with the optical microscope 602 is specified by using the optical microscope 202. This work may be manually performed by the user or may be automatically performed by a calculation process such as matching or similarity calculation based on the image acquired with the optical microscope 602. Next, the specimen is moved from the optical microscope 202 to the charged particle microscope 601 by the above method, and the specimen position specified with the optical microscope 202 is arranged in the irradiation position of the primary charged particle beam. Next, a transmitted charged particle image is acquired with the charged particle microscope. Accordingly, observation of the specimen position observed with the optical microscope outside the charged particle microscope device is very simple with the charged particle microscope by using the optical microscope 202 for positioning observation between the optical microscope outside the charged particle beam microscope device and the charged particle microscope.

The optical axis 200 of the charged particle microscope may be on the same axis as the optical axis 201 of the optical microscope 202 so that the location of the optical microscope 202 can be arranged immediately below the specimen base 500 as in FIG. 14. The optical axis 200 of the charged particle microscope and the optical axis 201 of the optical microscope 202 are on the same axis, and the same part can be observed. In addition, since both the optical microscope 602 and the optical microscope 202 are a microscope that uses light, observation of the same specimen part is very simple. Consequently, the same part as the specimen observed with the optical microscope 602 can be observed with the charged particle microscope 601 more easily than with the configuration in FIG. 13. In the case of observation with the optical microscope 202, the optical detector 503 may be detached, or the optical detector 503 may have a moving mechanism to be capable of changing the position thereof. In addition, the transmitted charged particle microscope image may be formed by acquiring light from the detecting element 500 via the optical microscope 202.

In addition, even in the case of FIG. 14, the optical microscope 202 can be used for positioning observation between the optical microscope outside the charged particle beam microscope device and the charged particle microscope as described in FIG. 13. In this case, achieved is an advantage that a step of moving the specimen from the optical microscope 202 to the charged particle microscope 601 is not required.

It may be difficult to immediately find a location observed with the optical microscope in the charged particle beam microscope. Therefore, next, means for sharing positional information between the optical microscope and the charged particle microscope will be described. As means for sharing positional information between microscopes, considered is a method of simply finding a location desired to be observed by using a mark on the specimen base. FIG. 15 illustrates a diagram of the detecting element 500, seen from the top, on which the specimen 6 is mounted. The detecting element 500 which is the specimen base includes a marking 913 that allows recognition of a positional relationship of the specimen with respect to the detecting element 500. The marking 913 is formed in a predetermined position in the specimen base and is, for example, a mark having a known pitch width like a ruler. The marking is made in the horizontal direction and in the vertical direction. Thus, a location that is observed can be recognized. In addition, in the case of having difficulty in marking on the detecting element 500, if the detecting element 500 is arranged on the base 501 that includes a marking, a location where the specimen is arranged on the specimen base can be recognized. In addition, a plurality of points of marks may be recorded on the specimen base, and the points may be used as reference points to recognize the observed position. For example, the specimen maybe used as a reference point. A work of storing the position of the specimen on the basis of the marking may be performed by the device user or may be performed on the higher control unit 36 or the like to create map data on the specimen base and find the position on the basis of the map data stored in a memory.

As described heretofore, the charged particle beam device, the specimen observation method, the specimen base, and the observation system in the present embodiment allow the three-dimensional internal structure of the specimen observed with the optical microscope to be observed with the charged particle microscope.

Embodiment 2

<Description of Principle of Three-Dimensional Observation>

In addition to the content described in FIGS. 6-2(a) to 6-2(d), a configuration of three-dimensional observation with increased measurement points by inclining the specimen 904 on the X axis and the Y axis will be described. Furthermore, a configuration of three-dimensional observation with increased measurement points by rotation about at least one of the X axis and the Y axis and a Z axis will be described. Accordingly, high-accuracy three-dimensional observation can be performed.

In addition, as another independent effect, a location that is difficult to be measured in one-directional observation can be measured by allowing observation of any location in the specimen from a plurality of angles.

In addition, as another independent effect, three-dimensional observation with increased measurement points can be performed at a relatively small inclination angle without observing the specimen and with significant inclination of a relative angle in order to increase the measurement point. Accordingly, significant inclination of the specimen is not required, and increase of the size of an inclining device for significant inclination or restrictions on spatial arrangement in the specimen chamber can be avoided.

A principle for performing three-dimensional observation of the specimen with use of the charged particle beam will be described by using FIGS. 16(a) to 16(c). That is, FIG. 16(a) illustrates a mutual relationship of the charged particle beam 905 with the specimen 904 at the time of being irradiated with the charged particle beam 905. Considered is irradiating the specimen 904 with the charged particle beam 905, scanning the charged particle beam 905 on the specimen, and consequently displaying a signal of an optical signal converted by the detecting element 500 as a microscope image on the monitor.

As illustrated in FIG. 16(a), internal substances 921, 922, and 923 exist inside the specimen 904. If the specimen 904 is considered to be a cell or the like, the internal substances 921, 922, and 923 correspond to organelles in the cell such as a cell nucleus, voids, and the like. The specimen is rotated about the Y axis on the detecting element 500. Rotation of the specimen changes the relative angle between the incident direction of the charged particle beam and the specimen, and a plurality of images with changed relative angles is acquired. The exterior of the specimen and three-dimensional positional arrangement of an internal structure of the specimen can be recognized on the basis of the plurality of images.

FIG. 16(a) illustrates a state of the specimen 904 being irradiated with the charged particle beam 905 before rotation of the specimen about the Y axis. In FIG. 16(a), a state of the specimen being seen from the same direction as the Y axis, which is the rotation axis, is illustrated. The optical axis of the charged particle beam 905 is a direction illustrated by an arrow. In addition, the X axis illustrates a line on the detecting element 500 that perpendicularly intersects with the Y axis which is the rotation axis.

A microscope image that is acquired in this state is illustrated in a lower part 925 of FIG. 16(a). In this drawing, the internal substance 921 partially overlaps with the internal substance 922 when viewed from the optical axis, and it is difficult to observe a part of the internal substance 922 in a state of not performing inclination.

The reason is exemplified by similarity between the numbers of charged particles scattered by the internal substance 921 and the internal substance 922 having similar density. In addition, the numbers of charged particles that are transmitted by each internal substance and reach the detecting element 500 are similar to each other. Consequently, there is almost no difference in brightness between the internal substance 921 and the internal substance 922 in the acquired microscope image. Thus, a vertical relationship between the internal substance 921 and the internal substance 922 cannot be identified. Furthermore, a vertical relationship between the internal substances 921 and 922 and the internal substance 923 cannot be identified.

Next, considered is irradiating the specimen 904 with the charged particle beam 905 slantwise in order to identify the exterior of the specimen 904 and the forms and the vertical relationship of the internal substances 921, 922, and 923. A state of inclining the specimen base 500 at the angle 0 by rotation about the X axis is illustrated in FIG. 16(c). A microscope image that is acquired at this point is a lower drawing (927) in FIG. 16(c).

If the drawing (927) is compared with a lower drawing (925) of the microscope image in FIG. 16(a), the internal substance 922 is not hidden in the internal substance 921 and is observed by inclination. In addition, the relative distances among the internal substances 921, 922, and 923 are changed. Furthermore, the size of the specimen 904 on the microscope image is changed. That is, comparing the image before inclination with the image after inclination and finding the amount of change of the specimen on the images allow observation of the three-dimensional structures of the specimen and the internal substances. Furthermore, acquiring images by successive rotation about the X axis or the Y axis allows recognition of the three-dimensional structure of the specimen in more detail. Displaying the acquired plurality of images in order on the monitor or lining up the plurality of images allows accurate identification of the three-dimensional structure of the specimen.

For example, given that a state of the specimen not being rotated is 0°, considered is acquiring images at each rotation angle by rotating the X axis at 10° at a time from −60° to +60°. The specified angular information is not particularly limited to these angles. In addition, the angular information may be stored in the system according to the property of the specimen or information desired to be observed.

A drawing of a stereographic projection of the relative angle between the specimen and the charged particle beam at the time of observation is illustrated by a set 240 of points in FIG. 17(a). While description is provided with a Wulff net, description can also be provided with a drawing of another stereographic projection. In this drawing, the relative angle of the charged particle beam with which the specimen is irradiated at the time of setting a circumference 250 as the specimen surface is illustrated by the set 240 of successive points. In order to recognize a three-dimensional structure in more detail, it is desirable to acquire images at each smallest possible angle.

In addition, while it is desirable to acquire images by inclination to the highest possible angle, the distance of the charged particle beam pas sing through the specimen is increased along with increase of the inclination angle. Thus, the number of charged particles scattered by the specimen, the internal substance, or the like is increased. Consequently, since the number of charged particles reaching the detecting element is decreased, a clear image may not be acquired in the case of observation by inclining the specimen at a high angle. Thus, in the case of an observation target that is a specimen extending on a horizontal surface as the specimen 904 in FIG. 16, observation may be typically performed with the upper limit of the inclination angle of approximately 50° to 70°. The present angles are merely one example. Preferable angles that are different according to the observed specimen are also included in the scope of the idea of the invention.

Furthermore, the acquired image may be subjected to tomography by computed tomography (CT). Subjecting the image to tomography allows display of the three-dimensional structure of the specimen by freely rotating the image on the monitor or allows display of only a cross section of the specimen. Accordingly, creating an image subjected to tomography can acquire a cross-sectional image or a slice image without slicing the specimen. In addition, another method may be used as a method for representing the inside information.

Next, a method for performing more accurate three-dimensional observation with two axes by increasing the rotation axis will be described. In the case of the specimen described in the present application, as described above, it is difficult to acquire a clear image in the case of increasing the inclination angle. Thus, the upper limit of the inclination angle at which a clear image is acquired is mostly 50° to 70°. Thus, it is difficult to acquire image information in the case of setting the inclination angle in the range from the upper limit angle to 90°. Accordingly, there exists a region in which it is hard to acquire an image, that is, an information missing region. For example, in the case of desiring to recognize an accurate three-dimensional structure, the information missing region is required to be decreased as far as possible. For example, in the case of desiring to measure the volume or the like of the specimen by subjecting images acquired by successive inclination to tomography, it is desirable to decrease the information missing region as far as possible.

As a method for decreasing the information missing region, a technique of observing the specimen from many directions by increasing the rotation axis to two axes will be described below. Considered is rotating the specimen on the detecting element 500 about the Y axis that is orthogonal with respect to the X axis, in addition to the rotation axis of the X axis. A mutual relationship among the specimen 904, the X axis, the Y axis, the charged particle beam 905, and the like is illustrated in FIG. 16(b).

FIG. 16(b) is a state of the specimen base 500 that is rotated about the Y axis as the rotation axis, inclined, and is irradiated with the charged particle beam 905 slantwise. A microscope image that is acquired in this state is a drawing 926 below FIG. 16(b). The distances among the internal substances 921, 922, and 923 and the exterior of the specimen 904 on the image are changed compared with 925 in FIG. 16(a) which is an image before inclination. In addition, the distances or a positional relationship among the internal substances 921, 922, and 923 and the exterior of the specimen 904 are changed compared with 927 in FIG. 16(c) which is an image acquired by inclining the specimen that is rotated about the X axis as the rotation axis. Accordingly, increasing the rotation axis from one axis to two axes allows observation from more directions, and the three-dimensional structure of the internal substance or the exterior of the specimen can be more accurately recognized.

Given that a state of the specimen not being rotated is 0°, a stereographic projection diagram that illustrates a relative positional relationship, at the time of acquisition of images at each rotation angle by rotating the Y axis at 10° at a time from −60° to +60°, between the specimen and the charged particle beam with which the specimen is irradiated is illustrated by a set 241 of points in FIG. 17(a). In addition to the set 240 of points indicating the relative irradiation angles between the specimen 904 and the charged particle beam with respect to the specimen in the case of the X axis as the rotation axis, the set 241 of points indicating the relative angle in the case of the Y axis as the rotation axis is distributed in a positional relationship that is orthogonal with respect to the set 240 of points. Adding the orthogonal Y axis as the rotation axis in addition to the X axis can decrease the information missing region. Accordingly, a more accurate three-dimensional structure can be recognized.

While independently rotating each of two rotation axes is considered heretofore, the two axes may be moved in connection with each other. For example, in FIG. 17(b) considered is acquiring images at each rotation angle by first performing rotation at +30° about the line segment of the X axis as the rotation axis and then performing rotation at 10° at a time from −60° to +60° about the Y axis as the rotation axis. The relative angles between the specimen and the charged particle beam in the acquired images are illustrated as a set 242 of points on a stereographic projection diagram (Wulff net) of FIG. 17(b). Accordingly, rotating two rotation axes in connection with each other allows observation from furthermore directions.

Furthermore, if inclination of each of the X axis and the Y axis from −60° to +60° is considered, the relative angle of the charged particle beam with which the specimen is irradiated can be freely changed inside a hatched portion 245 of a stereographic projection diagram (Wulff net) of FIG. 17(c). The specimen can be observed in the hatched portion 245 from various directions, and the three-dimensional structure of the specimen can be more accurately recognized.

While introduction of two rotation axes for inclining the specimen base is considered heretofore, a method that allows observation from many directions by introducing a rotation axis which allows rotation of the specimen on the plane of the specimen base with a direction perpendicular to the specimen base as an axis will be described by using FIG. 18.

FIG. 18 illustrates a mechanism capable of inclining the specimen base 500 about the X axis and a rotating mechanism capable of rotating the specimen on the plane of the specimen base with the Z axis that is orthogonal with respect to the specimen base 500 as a center. The X axis is considered to be operated independently of the Z axis. That is, even in the case of rotating the specimen about the Z axis, the X axis is not inclined, and only the specimen 904 or the specimen base 500 is rotated. Conversely, in the case of inclining the specimen about the X axis, the Z axis is also inclined with the specimen.

The case of inclining only the X axis without rotating the Z axis is the same as the case of one axis of the rotation axis. At this point, in the case of acquiring images at each rotation angle by rotation about the X axis at 10° from −60° to +60°, the relative angles between the specimen 904 and the charged particle beam 905 are the set 240 of points in a stereographic projection diagram of FIG. 18(a). The stereographic projection diagram is illustrated by a Schmidt net. This stereographic projection diagram illustrates the relative angle of the charged particle beam with which the specimen is irradiated at the time of setting the circumference 250 as the specimen surface.

Next, considered is rotating the specimen at 90° about the Z axis and then rotating the specimen about the X axis. This case is the same as the case of rotation about the Y axis in FIG. 18. In this state, in the case of acquiring images at each rotation angle by rotation at 10° at a time from −60° to +60° about the X axis as above, the relative angles between the specimen 904 and the charged particle beam 905 are the set 241 of points.

Furthermore, changing the rotation angle of the Z axis can increase the observation direction. For example, considered is acquiring images by clockwise rotation at 45° in a view from the direction of irradiation of the specimen with the charged particle beam and then rotation at 10° at a time from −60° to +60° about the X axis as above. The relative angles between the specimen and the charged particle beam at this point are a set 243 of points.

In addition, while rotation about the X axis after rotation about the Z axis is considered heretofore, the order of rotation may be reversed. For example, considered is acquiring images at each rotation angle by rotation at 45° about the X axis and then rotation of the Z axis at 10° at a time to 360°. If the relative angles between the specimen and the charged particle beam in the acquired images are illustrated on a stereographic projection diagram, a circular set 244 of points is acquired.

If rotating the X axis from −60° to +60° and rotating the Z axis from 0° to 90° is considered, the relative angle of the charged particle beam with which the specimen is irradiated can be freely changed inside the hatched portion 245 of a stereographic projection diagram (Schmidt net) of FIG. 19(*b*). Observing the specimen from various direction in the hatched portion 46 allows the three-dimensional structure of the specimen to be more accurately recognized. In addition, the information missing region can be significantly decreased.

<Description of Specimen Base>

The specimen base that allows the three-dimensional observation will be described below. A specimen base that allows observation from many directions by having two rotation axes about which the specimen can be inclined is illustrated in FIG. 20. A motor 810 is included on the specimen stage 500, and the specimen base 500 is configured to be fixed to a motor rotation shaft 811. The specimen stage 500 includes an inclination driving mechanism (angle control unit) that can perform inclination about an inclination axis 801. The motor 810 is arranged in such a manner that the motor rotation shaft 811 is orthogonal with respect to the inclination axis 801 of the specimen stage, and is fixed to the specimen stage 500 by a supporting member 805. The motor rotation shaft 811 includes a specimen holding member 812, and the specimen holding member 812 can be rotated along with the motor rotation shaft 811. The specimen base 500 that is attachably detachable and has the light-emitting member is attached to the specimen holding member 812. With the configuration heretofore, rotation on two axes can be performed by inclination of a specimen stage 800 and rotation of the motor 810.

Next, a specimen base that has a rotation axis allowing rotation of the specimen on the specimen stage and an inclination axis allowing inclination of the specimen is illustrated in FIG. 21. A rotation base 820 is included on the specimen stage 800, and the specimen base 500 that is attachably detachable and has the light-emitting member is attached onto the rotation base 820. The specimen stage 800 includes the inclination driving mechanism (angle control unit) that can perform inclination about the inclination axis 801. The rotation base 820 includes a rotation driving mechanism (angle control unit) that has a rotation axis in a direction orthogonal with respect to the specimen stage 800. The specimen base 500 attached onto the rotation base 820 can be rotated along with the rotation base 820. With the configuration heretofore, rotation on two axes can be performed by inclination by the specimen stage 800 and rotation of the rotation base 820. In addition, rotation (inclination) of two axes does not always require two driving units, and two axes can be controlled by using a motive power acquired from one driving unit.

In addition, although not illustrated, arranging a member exerting a rotational motion or a member changing a rotational motion into another motion between the motor 810 and the specimen base 500 can realize any of the above configurations regardless of the position of the motor 810. Examples of the member exerting a rotational motion include a gear, a chain, a belt, and the like. The member that changes a rotational motion into another motion is exemplified by a cam mechanism, a link mechanism, or the like.

Embodiment 3

The specimen base that is configured as a light-emitting element is described in Embodiment 1 or Embodiment 2. The present embodiment will describe the case of the specimen base that is a semiconductor detecting element capable of generating an electron and a positive hole if being irradiated with the charged particle beam. Hereinafter, the same parts as Embodiment 1 will not be described.

A principle and a configuration will be described by using FIG. 22. The specimen 6 is included on a specimen base 518 that is capable of generating an electron and a positive hole if being irradiated with the charged particle beam. The specimen base 501 is a semiconductor detecting element or the like, and a P layer, an N layer, a depletion layer, and the like exist in the specimen base 518. In this case, the specimen base 518 detects a charged particle scattered or transmitted through the specimen as in Embodiment 1. The detecting element that doubles as the specimen base includes thin layers such as an upper layer portion 512 and a lower layer portion 513. These thin layers are materials allowing flowing of electricity and are, for example, metal films. While the thin layers are described on the entire surface of the drawing, the thin layers may be in a part of the drawing.

Considered is the case of the specimen having a high-density part 508 and a low-density part 509. In the case of irradiating the high-density part 508 in the specimen with the primary charged particle beam 510, most of the charged particle beam is backscattered. Thus, the charged particle beam does not reach the detecting element 518. Meanwhile, in the case of irradiating the low-density part 509 in the specimen with the primary charged particle beam 511, the charged particle beam can be transmitted to the detecting element 518. The charged particle beam that reaches the detecting element 518 generates a positive electron hole pair 514 inside the detecting element 518. Generation of the positive electron hole pair 514 causes a positive hole or an electron to be attracted to the upper layer portion 512 and the lower layer portion 513. If a resistor 515 that is outside the present detecting element doubling as the specimen base is connected between the upper layer portion 512 and the lower layer portion 513 through an interconnect 516 or the like, the above positive electron pair allows the current I to flow therebetween. Consequently, a voltage V is generated across the resistor 515. Amplifying the voltage V with an amplifier 517 can amplify a signal. Consequently, a difference in density inside the specimen can be detected by acquiring a signal from the detecting element 518.

The inelastic mean free path of the charged particle beam is a few tens of nm to a few tens of μm, though depending on an accelerating voltage of the charged particle beam. Thus, the thickness of the upper layer portion 512 on the upper surface of the detecting element 518 is required to be approximately the same thickness. In addition, while the specimen 6 is in contact with the upper layer portion 512 in the drawing, a specimen may not be mounted on the upper layer portion 512 in terms of toxicity or the like in the case of the specimen being a biological specimen or the like. Therefore, a material that has high affinity with a biological specimen, such as collagen, may be applied. The material may be arranged between the upper layer portion 512 and the specimen 6.

In addition, as described in Embodiment 1, in the case of the specimen 6 being a hydrated specimen or the like, the thin film 702 may be arranged around the specimen, or moisture inside the specimen may be used as the replacement substance 703 such as an ionic liquid.

FIGS. 17(a) to 17(c) illustrate a device configuration for performing three-dimensional internal structure observation with use of the semiconductor detecting element of the present embodiment. In FIG. 23, the semiconductor detecting element 518 that is a specimen base is arranged on the specimen stage 5. The preamplifier substrate 505 is connected via the interconnect 509 to the detecting element 518 included in the stage 5. The preamplifier substrate 505 is connected to the lower control unit 37 via the interconnect 507 and the like. While the preamplifier substrate 505 is inside the casing 7 in the drawing, the preamplifier substrate 505 may be outside the casing 7 (for example, the preamplifier 54 in the drawing). The specimen base 518 is required not to fall from the specimen stage 5 at the time of inclining the specimen base 518. Thus, the fixing member 506 that can determine a position to arrange the specimen base 518 is included on the specimen stage 5. In addition, a fixing member not illustrated may be between the specimen base 518 and the specimen stage 5. Accordingly, the specimen base 518 can be fixed, and positional shift thereof can be prevented. When the specimen base is introduced into the device or taken outside of the device, the specimen base 518 is attached or detached with respect to the specimen stage 5 by connecting or detaching the interconnect 509.

In addition, the present embodiment can be realized with a micro-channel plate (MCP) or another particle detector. While a specific device configuration is not provided, the present embodiment can be realized with a configuration that is equivalent to the content described in the present embodiment except that a photoelectric conversion part or an interconnect is different.

Embodiment 4

"Atmospheric pressure" in an embodiment below means an atmospheric pressure environment or a pressure environment in a state of a slightly negative pressure in the atmosphere or in a predetermined gas atmosphere. Specifically, the atmospheric pressure is approximately $10^5$ Pa (atmospheric pressure) to $10^3$ Pa.

<Description of Charged Particle Beam Device Observation Under Atmospheric Pressure>

Next, an example that uses a charged particle beam device capable of observation under the atmospheric pressure will be described by using FIG. 24. A basic configuration of the charged particle microscope is the same as described in Embodiment 1 (for example, the configuration in FIG. 7-1) and Embodiment 2. Thus, only a feature of an atmospheric pressure observation device will be mainly described in the present embodiment.

FIG. 24 illustrates an entire configuration of the charged particle microscope of the present embodiment. In the present configuration, the charged particle optical column 2 is embedded in a casing 271 and is sealed in a vacuum by the vacuum seal member 123. The casing 271 is supported by a post 269. The post 269 is supported by a base 270. While only one post 269 is illustrated in the drawing, the post 269 is preferably in plural numbers in actuality to support the casing. With this configuration, an atmospheric state of the specimen 6 is equivalent to the outside of the device. Thus, the state of the specimen can be exposed to a state of the complete atmosphere.

A partitioning film 10 through which the charged particle beam can be transmitted or passed is disposed between the charged particle optical column and the specimen. The partitioning film 10 can be attached and detached with respect to the casing 271. The vacuum pump 4 is connected to the casing 271 to allow evacuation of a closed space (hereinafter, referred to as a first space) that is configured of inner wall surfaces of the casing 271 and the partitioning film 10. Accordingly, in the present embodiment, a first space 11 is maintained in a high vacuum by the partitioning film 10, and a space in which the specimen is mounted is maintained in a gas atmosphere having the atmospheric pressure or an almost equivalent pressure as the atmospheric pressure. Thus, during operation of the device, the charged particle optical column 2 side can be maintained in a vacuum state, and the specimen 6 and the above specimen base can be maintained in an atmosphere having the atmospheric pressure or a predetermined pressure. The partitioning film 10 is held by a partitioning film holding member 155, and the partitioning film 10 can be replaced by replacing the partitioning film holding member 155.

A gas nozzle 272 supplies gas from a gas cylinder 103 in a direction to near the specimen 6. The gas nozzle 272 is connected to the casing 271 by, for example, a support 273. The gas cylinder 103 and the gas nozzle 272 are connected by a connecting unit 102. The above configuration is merely one example. Desired gas can be ejected to near the specimen 6 by the present configuration. Types of gas include nitrogen that is lighter than the atmosphere, vapor, helium gas, hydrogen gas, and the like that can reduce scattering of an electron beam. The user can freely replace the gas. In addition, the gas cylinder 103 may be replaced with a vacuum pump in order to make a vacuum between the partitioning film 10 and the specimen 6.

An optical microscope 250 is arranged immediately below the casing 271, that is, on the same axis as the optical axis of the charged particle optical column. Accordingly, a charged particle beam microscope image can be acquired by irradiating the specimen 6 on the specimen base arranged on the specimen stage 5 with the charged particle beam passing the partitioning film 10, and an optical microscope image can be acquired with the optical microscope 250. Arrangement of the optical microscope is not limited thereto as in the above embodiments.

The specimen base that includes the detecting element 500 can be mounted on the specimen stage 5 of the present charged particle beam device. In a state of the above specimen base being mounted on the specimen stage, the detecting element 500 is in a state of being mounted on the opposite side of the specimen from the partitioning film. The arrangement configuration and the like of the optical detector 503 and the like near the specimen stage are the same as Embodiments 1 and 2. In the case of the present configuration, acquisition of a transmitted charged particle beam signal in which shape change such as moisture evaporation generated by making of a vacuum or the like is reduced to the maximum extent can be performed. In addition, since a high vacuum is not required to be made in the specimen space, a transmitted charged particle beam microscope image of the specimen can be acquired with very high throughput. In addition, since there is no restriction on the specimen arrangement space in the configuration of the present embodiment, the present embodiment is useful in the case of the specimen base having a very large size.

Embodiment 5

Next, a side entry type device configuration into which the specimen and the specimen base are introduced from a small region in a side surface of the casing 7 will be described by using FIG. 25. Hereinafter, the same parts as Embodiments 1 to 3 will not be described.

The specimen stage 5 is introduced into the device so as to be inserted from a narrow region of a part of the casing 7. A control system for controlling each optical lens, a detection system for detecting a detected signal, a vacuum pump for evacuating the inside of the casing 7 or the charged particle optical column 2, and the like are apparent and thus are not illustrated. Light emission from the detecting element 500 on which the specimen 6 is directly or indirectly mounted is detected through a light transmission path 801 in the optical detector 800 that is arranged inside the casing 7 or the like. The optical detector for detecting light emission from the detecting element 500 is preferably arranged inside or outside the casing 7 or in any of the specimen base 7, the specimen stage 5, and the optical column 2 in the drawing. Positions and modification examples of the optical amplifier and the light transmission path fall within the scope of the charged particle beam microscope of the present embodiment as long as satisfying the function intended in the present embodiment. In the present configuration, a mechanism that can incline, for example, the specimen angle θ which is the vector parameter is included in the specimen stage 5. In the case of the present configuration, the size of the specimen stage 5 can be decreased compared with the above embodiment. Thus, the inclining mechanism on the specimen stage 5 can be significantly simplified.

The invention is not limited to the above embodiments and includes various modification examples to the extent not departing from the technical idea of the present application. For example, the above embodiments are described in detail for describing the invention in an easy understanding manner, and the invention is not limited to an embodiment that includes all configurations described. In addition, a part of the configuration of one embodiment can be replaced with the configuration of another embodiment, and the configuration of another embodiment can be added to the configuration of one embodiment. In addition, addition of another configuration, removal, or replacement with respect to a part of the configuration of each embodiment can be performed. In addition, a part or all of each configuration, function, processing unit, processing means, and the like above may be realized by hardware by, for example, designing in an integrated circuit. In addition, each configuration, function, and the like above may be realized by software by a processor interpreting and executing a program that realizes each function. Information of the program, tables, files, and the like realizing each function can be placed in a recording device such as a memory, a hard disk, or a solid state drive (SSD) or in a recording medium such as an IC card, an SD card, or an optical disc.

In addition, the counting process and the signal calculation process described above can be realized by a software program code that realizes these functions. In this case, the system or the computer (or a CPU or an MPU) of the device reads the program code stored in a storage medium. In this case, the program code read from the storage medium realizes the functions of the embodiments described above, and the program code and the storage medium storing the program code constitute the invention.

In addition, a control line and an information line are illustrated if being considered to be required for description, and not all control lines and information lines of a product are illustrated. In actuality, almost all configurations may be considered to be connected to each other.

REFERENCE SIGNS LIST

1 OPTICAL LENS
2 CHARGED PARTICLE OPTICAL COLUMN
3 DETECTOR
4 VACUUM PUMP
5 SPECIMEN STAGE
6 SPECIMEN
7 CASING
8 CHARGED PARTICLE SOURCE
10 PARTITIONING FILM
11 FIRST SPACE
14 LEAK VALVE
16 VACUUM PIPE
18 SUPPORTING POST
19 LID MEMBER SUPPORTING MEMBER
20 BOTTOM PLATE
34 USER INTERFACE SUCH AS KEYBOARD OR MOUSE
35 MONITOR
36 HIGHER CONTROL UNIT
37 LOWER CONTROL UNIT
38 STAGE CONTROL UNIT
39 COMMUNICATION LINE
40 DATA SENDING AND RECEIVING UNIT
41 DATA MEMORY UNIT
42 EXTERNAL INTERFACE
43 CALCULATING UNIT
44 OPERATING SCREEN
45 IRRADIATION ENERGY CHANGING UNIT
46 IRRADIATION ANGLE CHANGING UNIT
47 SPECIMEN ANGLE CHANGING UNIT
48 FOCAL POINT ADJUSTING UNIT
49 BRIGHTNESS ADJUSTING UNIT
50 CONTRAST ADJUSTING UNIT
51 IRRADIATION START BUTTON
52 IRRADIATION STOP BUTTON
53 PREAMPLIFIER
54 PREAMPLIFIER
55 SCREEN
56 SCREEN
57 IMAGE STORE BUTTON
58 IMAGE READ BUTTON
59 IRRADIATION ENERGY CONTROL UNIT
60 SPECIMEN ROTATION ANGLE CONTROL UNIT
61, 62, 63, 64, 65, 66, 67 STEP
70 OPERATING SCREEN
71 INITIAL SPECIMEN ANGLE θ SETTING UNIT
72 FINAL SPECIMEN ANGLE θ SETTING UNIT
73 CHANGED ANGLE Δθ SETTING UNIT
74 VERTICAL SETTING BAR
75 HORIZONTAL SETTING BAR
76 SCREEN
77 AUTOMATIC IMAGE ACQUISITION REFERENCE POINT
78 AUTOMATIC ACQUISITION START BUTTON
102 CONNECTING UNIT
103 GAS CYLINDER
107 SUPPORTING PLATE
119 HERMETIC SEAL
120 HERMETIC SEAL
122 LID MEMBER
123, 124, 125, 126, 128, 129 VACUUM SEAL MEMBER

155 PARTITIONING FILM HOLDING MEMBER
200 OPTICAL AXIS OF CHARGED PARTICLE MICROSCOPE
201 OPTICAL AXIS OF OPTICAL MICROSCOPE
202 OPTICAL MICROSCOPE
250 OPTICAL MICROSCOPE
269 POST
270 BASE
271 CASING
272 GAS NOZZLE
500 SPECIMEN BASE OR DETECTING ELEMENT
501 BASE
502 THIN FILM
503 OPTICAL DETECTOR
505 PREAMPLIFIER SUBSTRATE
506 FIXING MEMBER
507 INTERCONNECT
508 HIGH-DENSITY PART
509 LOW-DENSITY PART
510 PRIMARY CHARGED PARTICLE BEAM
511 PRIMARY CHARGED PARTICLE BEAM
512 UPPER LAYER PORTION
513 LOWER LAYER PORTION
514 POSITIVE ELECTRON HOLE PAIR
515 RESISTOR
516 INTERCONNECT
517 AMPLIFIER
518 DETECTING ELEMENT
601 CHARGED PARTICLE BEAM MICROSCOPE
602 OPTICAL MICROSCOPE
603 CCD CAMERA
604 INTERCONNECT
702 THIN FILM
703 REPLACEMENT SUBSTANCE
800 OPTICAL DETECTOR
801 LIGHT TRANSMISSION PATH
810 MOTOR
811 MOTOR ROTATION SHAFT
820 ROTATION BASE
900 CHARGED PARTICLE BEAM
901 INTERNAL STRUCTURE
902 INTERNAL STRUCTURE
903 INTERNAL STRUCTURE
903a PROJECTED INTERNAL STRUCTURE
903, 904 SUBSTANCE
905 OPTICAL AXIS
906 PROJECTED IMAGE (OR DETECTED IMAGE)
907 PROJECTED IMAGE (OR DETECTED IMAGE)
908 PROJECTED IMAGE (OR DETECTED IMAGE)
909 GOLD LABEL
910 PROJECTED IMAGE (OR DETECTED IMAGE)
911 GOLD LABEL
912 PROJECTED IMAGE (OR DETECTED IMAGE)
913 MARKING
914 SPECIMEN INTERNAL STRUCTURE
915 PROJECTED IMAGE (OR DETECTED IMAGE)
916 PROJECTED IMAGE (OR DETECTED IMAGE)
917 PROJECTED IMAGE (OR DETECTED IMAGE)
918 PROJECTED IMAGE (OR DETECTED IMAGE)
921, 922, 923 INTERNAL SUBSTANCE

The invention claimed is:

1. A charged particle beam device comprising:
a charged particle optical column that irradiates a specimen held in a specimen base with a primary charged particle beam;
a specimen base rotating unit that is capable of rotating the specimen base in a state of an angle formed by a surface of the specimen base and an optical axis of the primary charged particle beam being inclined to a non-perpendicular angle; and
a control unit that controls a rotation angle of the specimen base rotating unit,
wherein the specimen base is configured to include a detecting element that detects a charged particle scattered or transmitted inside the specimen, and
transmitted charged particle images of the specimen corresponding to each angle is acquired by irradiating the specimen with the primary charged particle beam in a state of the specimen base rotating unit being rotated at a plurality of different angles.

2. The charged particle beam device according to claim 1, further comprising:
a specimen stage in which the specimen base is arranged in an attachably detachable manner,
wherein the specimen stage has a specimen base inclining unit that is capable of inclining the specimen base at a plurality of different angles.

3. The charged particle beam device according to claim 1, further comprising:
an optical lens that inclines the primary charged particle beam with respect to the optical axis of the primary charged particle beam and causes the primary charged particle beam to be incident on the specimen.

4. The charged particle beam device according to claim 1, further comprising:
a monitor that displays a plurality of transmitted charged particle images corresponding to each of the angles by switching the plurality of transmitted charged particle images in each any amount of time in order of magnitude of each of the angles.

5. The charged particle beam device according to claim 1, wherein the detecting element is a light-emitting member that emits light by the charged particle transmitted or scattered inside the specimen.

6. The charged particle beam device according to claim 5, wherein the light-emitting member is capable of allowing passage of visible light, ultraviolet light, or infrared light in a specific or all wavelength regions.

7. The charged particle beam device according to claim 1, further comprising:
an attachably detachable partitioning film that allows transmission or passage of the primary charged particle beam,
wherein the partitioning film isolates an internal space of the charged particle optical column from a space in which the specimen is mounted.

8. A charged particle beam device comprising:
a charged particle optical column that irradiates a specimen held in a specimen base with a primary charged particle beam;
a specimen stage in which the specimen base is arranged in an attachably detachable manner; and
an angle control unit that controls a relative angle between the primary charged particle beam and the specimen with a first axis and a second axis different from the first axis,
wherein the specimen base is configured to include a detector that detects a charged particle scattered or transmitted inside the specimen, and
transmitted charged particle images of the specimen corresponding to each relative angle are acquired by performing irradiation with the primary charged particle beam at a plurality of the different relative angles in the first axis and in the second axis.

9. The charged particle beam device according to claim 8, wherein the angle control unit has a first axis angle control unit that controls the relative angle between the primary charged particle beam and the specimen with the first axis, and a second axis angle control unit that controls the relative angle between the primary charged particle beam and the specimen with the second axis different from the first axis.

10. The charged particle beam device according to claim 9, wherein the second axis angle control unit makes a rotational motion around a center of the second axis that is not parallel to a horizontal plane of the specimen base, and controls the relative angle between the primary charged particle beam and the specimen by rotating the specimen base with the rotational motion.

11. The charged particle beam device according to claim 8, wherein the specimen inclining unit controls the relative angle between the primary charged particle beam and the specimen by any one or a combination of two or more of inclination of the charged particle optical column, beam tilt of the primary charged particle beam, inclination of the specimen stage, and inclination of the specimen base.

12. The charged particle beam device according to claim 8, further comprising:
a display unit that displays the acquired transmitted charged particle images of the specimen corresponding to each relative angle by computed tomography; and
a selection input unit that displays a rotation diagram or a cross-sectional view of the image by allowing selection of a part of the displayed transmitted charged particle images of the specimen.

13. A charged particle beam device comprising:
a charged particle optical column that irradiates a specimen held in a specimen base with a primary charged particle beam;
a specimen stage in which the specimen base is arranged in an attachably detachable manner;
a specimen base inclining unit that inclines an angle formed by a surface of the specimen base and an optical axis of the primary charged particle beam to a non-perpendicular angle with an inclination axis different from an inclination axis of the specimen stage; and
a control unit that controls an inclination angle of the specimen base inclining unit,
wherein the specimen base is configured to include a detecting unit that detects a charged particle scattered or transmitted inside the specimen, and
transmitted charged particle images of the specimen corresponding to each relative angle are acquired by inclining the specimen base at a plurality of the different relative angles with the inclination axis different from the specimen stage and by irradiating the specimen with the primary charged particle beam.

14. The charged particle beam device according to claim 13, wherein, in a case of the specimen stage having an inclining mechanism, the specimen base inclining unit is capable of performing inclination at a larger angle than a movable range of the specimen stage.

15. The charged particle beam device according to claim 13, wherein the detecting unit is a light-emitting member that emits light by the charged particle transmitted or scattered inside the specimen.

* * * * *